United States Patent [19]

Ono et al.

[11] Patent Number: 5,573,945
[45] Date of Patent: Nov. 12, 1996

[54] MUTANT AND METHOD FOR PRODUCING L-GLUTAMIC ACID BY FERMENTATION

[75] Inventors: Eiji Ono; Nobuharu Tsujimoto; Kazuhiko Matsui; Osamu Kurahashi, all of Kawasaki, Japan

[73] Assignee: Ajinomoto Co., Inc., Tokyo, Japan

[21] Appl. No.: 370,193

[22] Filed: Jan. 9, 1995

[30] Foreign Application Priority Data

Jan. 10, 1994 [JP] Japan .................................. 6-000825

[51] Int. Cl.$^6$ .......................... C12N 1/21; C12N 15/67; C12N 15/70; C12P 13/14
[52] U.S. Cl. .................... 435/252.33; 435/110; 435/244; 935/33; 935/38; 935/73
[58] Field of Search ............................. 435/252.33, 244, 435/813, 849, 848, 110; 935/33, 22, 38, 23, 39, 44, 66, 72, 73

[56] References Cited

U.S. PATENT DOCUMENTS

| | | | |
|---|---|---|---|
| 3,663,370 | 5/1972 | Kono et al. | 435/110 |
| 4,347,318 | 8/1982 | Miwa et al. | 435/115 |
| 4,411,991 | 10/1983 | Hirakawa et al. | 435/42 |
| 4,729,952 | 3/1988 | Hattori et al. | 435/110 |
| 4,757,009 | 7/1988 | Sano et al. | 435/106 |
| 5,378,616 | 1/1995 | Tujimoto et al. | 435/110 |

FOREIGN PATENT DOCUMENTS

| | | |
|---|---|---|
| 8693 | 1/1981 | Japan . |
| 8694 | 1/1981 | Japan . |
| 20194 | 2/1983 | Japan . |

*Primary Examiner*—Mindy Fleisher
*Assistant Examiner*—Nancy J. Degen
*Attorney, Agent, or Firm*—Oblon, Spivak, McClelland, Maier & Neustadt, P.C.

[57] ABSTRACT

A mutant of the genus Escherichia is described, the α-ketoglutarate dehydrogenase activity of which is deficient or reduced, and/or the phosphoenol pyruvate carboxylase and/or glutamate dehydrogenase activities of which are amplified. The mutant is useful in the fermentative production of L-glutamic acid.

6 Claims, 3 Drawing Sheets

MUTANT AND METHOD FOR PRODUCING L-GLUTAMIC ACID BY FERMENTATION

SUMMARY OF THE INVENTION

1. Field of the Invention

The present invention concerns a mutant useful in producing L-glutamic acid by fermentation, as well as a method of producing L-glutamic acid by fermentation using such a mutant. L-glutamic acid is an amino acid used in foods and medicaments.

2. Discussion of the Background

L-glutamic acid has conventionally been produced by fermentation using glutamic acid-producing bacteria and mutants thereof, such as those of the genus Brevibacterium, Corynebacterium or Microbacterium ("Amino Acid Fermentation," Gakkai Shuppan Center, pp. 195 to 215 (1986)). Other known methods of producing L-glutamic acid by fermentation include those employing microorganisms of the genera Bacillus, Streptomyces or Penicillium (U.S. Pat. No. 3,220,929) and microorganisms of the genera Pseudomonas, Arthrobacter, Serratia or Candida (U.S. Pat. No. 3,563,857). Even though such conventional methods produce significant amounts of L-glutamic acid, a more efficient and less expensive method of producing L-glutamic acid is desired in order to meet the ever-increasing demand.

*Escherichia coli* is potentially an excellent L-glutamic acid-producing bacterium, in view of (a) its high growth rate and (b) the availability of sufficient genetic information. However, the reported amount of L-glutamic acid production by *Escherichia coli* is as low as 2.3 g/l (J. Biochem., Vol. 50, pp. 164 to 165 (1961)). Recently, a mutant exhibiting a deficient or reduced α-ketoglutarate dehydrogenase (hereinafter referred to as α-KGDH) was reported to have the ability to produce large amounts of L-glutamic acid (French Patent Application Laid-Open No. 2680178).

SUMMARY OF THE INVENTION

Accordingly, one object of the present invention is to enhance the L-glutamic acid-producing ability of strains belonging to the genus Escherichia.

A further object of the present invention is to provide a method of producing L-glutamic acid more efficiently and at a lower cost than prior methods.

These and other objects, which will become apparent during the following detailed description of the preferred embodiments, have been surprisingly provided by a mutant of *Escherichia coli*, the α-KGDH activity of which is deficient or reduced, and the phosphoenolpyruvate carboxylase (hereinafter referred to as PPC) and glutamate dehydrogenase (hereinafter referred to as GDH) activities of which are amplified.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
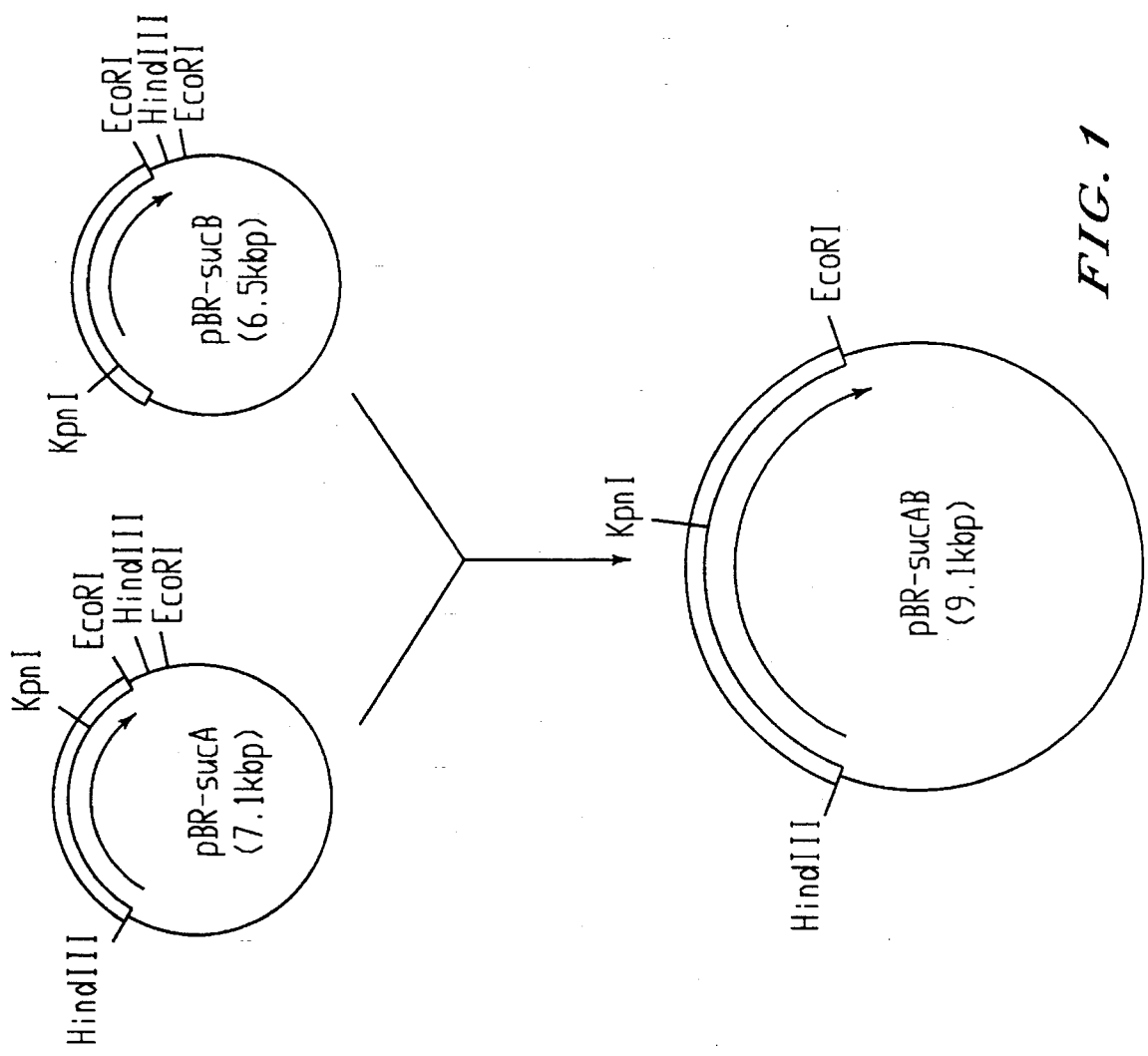
FIG. 1 shows the procedure for constructing pBR-sucAB.

Accordingly, the present invention includes a mutant of the genus Escherichia which produces L-glutamic acid, the α-KGDH activity of which is deficient or reduced, and the PPC and GDH activities of which are amplified; and a method of producing L-glutamic acid by fermentation comprising (a) culturing in a liquid culture medium a mutant of the genus Escherichia which produces L-glutamic acid, the α-KGDH activity of which is deficient or reduced and the PPC and GDH activities of which are amplified, (b) accumulating L-glutamic acid in the culture medium, and (c) recovering L-glutamic acid therefrom.

In accordance with the present invention, a mutant of the genus Escherichia which exhibits deficient, reduced and/or amplified activity refers to deficient, reduced and/or amplified activity relative to the starting strain (e.g., *E. coli* K-12 (ATCC 10798), W3110 (ATCC 27325), B (ATCC 11303) or W (ATCC 9637)), a wild-type (naturally-occurring) strain or a non-pathogenic strain of the genus Escherichia.

The present invention is detailed below.

(1) Derivation of a mutant of the genus Escherichia exhibiting deficient or reduced α-KGDH activity Any non-pathogenic strains of the genus Escherichia may be employed as a starting parent strain to be used in preparation of the present mutant. Examples of such non-pathogenic strains include:

(1) *Escherichia coli* K-12 (ATCC 10798)

(2) *Escherichia coli* W3110 (ATCC 27325)

(3) *Escherichia coli* B (ATCC 11303)

(4) *Escherichia coli* W (ATCC 9637)

A mutant of the genus Escherichia which produces L-glutamic acid and which has deficient or reduced α-KGDH activity may be prepared in accordance with known procedures (e.g., Maniatis et al, "Molecular Cloning," Cold Spring Harbor Laboratories, Cold Spring Harbor, Mass. (1989)), or may be prepared as follows.

A non-pathogenic starting parent strain of the genus Escherichia (e.g., one of those mentioned above) may be exposed to X-radiation, ultraviolet light, or one or more mutagenic agents such as N-methyl-N'-nitro-N-nitrosoguanidine (hereinafter referred to as NG) to introduce a mutation in the genetic material of the parent strain.

Alternatively, gene engineering technology, for example, gene recombination, gene transformation or cell fusion, may be used to efficiently introduce the intended mutation. A method of obtaining an α-KGDH-deficient mutant by gene recombination is conducted as follows.

Based on the known nucleotide sequence of the *E. coli* α-ketoglutarate decarboxylase gene (hereinafter referred to as the sucA gene; see *Euro. J. Biochem.*, Vol. 141, pp. 351 to 359 (1984)), primers corresponding to nucleotide sequences at or near the 5'- and 3'-termini may be designed and synthesized. Thereafter, the sucA gene is amplified by PCR using the chromosomal DNA as a template. Into the amplified sucA gene, a drug-resistance gene is inserted to obtain a sucA gene whose function is lost. Subsequent homologous recombination replaces the sucA gene on the chromosome with a sucA gene whose function is lost as a result of insertion of the drug-resistance gene.

After subjecting the parent strain to mutagenic treatment, the intended mutants may be screened by known techniques for identifying such mutants by their biological properties or by the procedures illustrated below.

A mutant exhibiting deficient or reduced α-KGDH activity is either not able to grow or is able to grow only at a significantly reduced growth rate under aerobic conditions in a minimum culture medium containing glucose as the carbon source. However, even under such conditions, normal growth is possible by either (a) adding succinic acid or (b) lysine plus methionine to the minimum culture medium containing glucose. On the other hand, anaerobic conditions allow the mutant to grow even in the minimum culture medium containing only glucose as a carbon source (*Molec. Gen. Genetics*, Vol. 105, pp. 182 to 190 (1969)). Based on these findings, the desired mutants can be screened and/or identified.

An example of the mutants thus obtained having deficient or reduced α-KGDH activity is *Escherichia coli* W3110 sucA::Km$^r$.

A mutant whose α-KGDH activity is deficient or reduced is more useful in view of its enhanced ability to produce L-glutamic acid when it further has either reduced L-glutamic acid-degrading activity or constitutive expression of the ace operon (i.e., malate synthase (aceB)-isocitrate lyase (aceA)isocitrate dehydrogenase kinase/phosphatase (aceK)). These properties are discussed in French Patent Application Laid-open No. 2680178. As a matter of course, properties already known to be effective for improving L-glutamic acid-productivity, such as various types of auxotrophy, antimetabolite resistance and antimetabolite sensitivity, are also desirable for enhancing L-glutamic acid production ability.

A mutant having a reduced ability to degrade L-glutamic acid may be isolated as a mutant which either cannot grow or can grow only slightly in a minimum culture medium containing L-glutamic acid as the sole carbon source (e.g., instead of glucose) or as a sole nitrogen source (e.g., instead of ammonium sulfate). However, as a matter of course, when an auxotroph is employed for the derivation, the minimum essential amount of the nutrient required for growth of the auxotroph may be added to the culture medium.

A mutant in which the expression of the ace operon is constitutive may be obtained as a strain whose parent strain is a phosphoenolpyruvate synthase-deficient strain and which can grow in a minimum culture medium containing lactic acid as the carbon source, but which cannot grow in a minimum culture medium containing pyruvic acid (and optional, further containing acetic acid) as the carbon source. Alternatively, a mutant which constitutively expresses the ace operon can be obtained as a strain which shows a higher growth rate than that of its parent strain, the α-KGDH activity of which is deficient or reduced under aerobic conditions (*J. Bacteriol.*, Vol. 96, pp. 2185 to 2186 (1968)).

Examples of the mutants described above include *Escherichia coli* AJ 12628 (FERM BP-3854) and *Escherichia coli* AJ 12624 (FERM BP-3853).

*Escherichia coli* AJ 12628 is a mutant which constitutively expresses the ace operon and has a reduced α-KGDH activity and a reduced ability to degrade L-glutamic acid. *Escherichia coli* AJ 12624 is a mutant having reduced α-KGDH activity and a reduced ability to degrade L-glutamic acid (French Patent Application Laid-open No. 2680178).

In the mutant thus obtained which exhibits deficient or reduced α-KGDH activity, the biosynthesis of L-glutamic acid via a-ketoglutaric acid in the TCA cycle is improved, resulting in an enhanced ability to produce L-glutamic acid. Also, the productivity of L-glutamic acid is increased in both (1) the mutant exhibiting deficient or reduced eα-KGDH activity and significantly lower ability to degrade the produced L-glutamic acid and (2) the mutant further constitutively expressing the ace operon, whereby its growth is improved.

(2) Derivation of a mutant of the genus Escherichia having amplified PPC activity and GDH activity In the examples described below, a mutant of the genus Escherichia having amplified PPC and GDH activities was obtained from a starting parent strain having (1) the ability to produce L-glutamic acid and (2) deficient or reduced α-KGDH activity. It is also possible to use a wild strain of the genus Escherichia as the parent strain to first obtain a mutant having amplified PPC and GDH activities, then breed a mutant therefrom which exhibits deficient or reduced α-KGDH activity.

Accordingly, the starting parent strain used to prepare a mutant having amplified PPC and GDH activities is preferably (a) a mutant of the genus Escherichia which produces L-glutamic acid and which exhibits deficient or reduced α-KGDH activity, or (b) a non-pathogenic wild-type strain of the genus Escherichia. Examples of such strains include *Escherichia coli* W3100 sucA::Km$^r$, *Escherichia coli* AJ 12628 (FERM BP-3854) and *Escherichia coli* AJ 12624 (FERM BP-3853) (L-glutamic acid-producing mutants whose α-KGDH activity is deficient or reduced); *Escherichia coli* K-12 (ATCC 10798), *Escherichia coli* W3110 (ATCC 27325), *Escherichia coli* B (ATCC 11303) and *Escherichia coli* W (ATCC 9637) (non-pathogenic wild strains of the genus Escherichia).

In order to amplify PPC and GDH activities, the genes coding for PPC and GDH are cloned on an appropriate plasmid, which is then used to transform the starting parent strain employed as a host. The copies of the genes coding for PPC and GDH (hereinafter referred to as the ppc gene and the gdhA gene, respectively) in the transformed cells are increased, resulting in amplified PPC and GDH activities.

The ppc and gdhA genes may be cloned into a single plasmid to be introduced into the starting parent strain employed as the host, or may be cloned separately into two types of plasmid which are compatible in the starting parent strain.

Alternatively, the amplification of PPC and GDH activities may be conducted by allowing the ppc and gdhA genes to be present as multicopies on the chromosomal DNA of the starting parent strain employed as the host. In order to introduce the ppc and gdhA genes as multicopies into the chromosomal DNA of the genus Escherichia, homologous recombination is applied utilizing a target sequence present as a multicopy on the chromosomal DNA. The sequence present as the multicopy may be a repetitive DNA and an inverted repeat present at the terminal of insertion sequence. Alternatively, as described in Japanese Patent Application Laid-open No. 2-109985, the ppc and gdhA genes may be cloned on a transposon, which is then transposed, thereby introducing the multicopy into the chromosomal DNA. The number of copies of the ppc and gdhA genes in the transformed cells are thus increased, resulting in amplification of PPC and GDH activities.

In addition to the gene amplification techniques described above, the amplification of PPC and GDH activities may also be conducted by replacing the promoters of the ppc and gdhA genes with those having higher potencies. For example, the lac promoter, trp promoter, trc promoter, tac promoter and the lambda phage $P_R$ and $P_L$ promoters are known to be strong promoters. By enhancing expression of the ppc and/or gdhA genes, the PPC and/or GDH activities may be amplified.

The ppc and gdhA genes can be obtained by isolating the genes which are complementary with regard to auxotrophy of the mutants which are either PPC- or GDH-deficient. Alternatively, since the nucleotide sequences of these genes of *Escherichia coli* are known (*J. Biochem.*, Vol. 95, pp. 909 to 916 (1984); Gene, Vol. 27, pp. 193 to 199 (1984)), the primers may be designed and synthesized based on the nucleotide sequences, and then the genes may be obtained by PCR, using the chromosomal DNA as a template.

(3) Production of L-glutamic acid by fermentation using an L-glutamic acid-producing mutant of the genus Escherichia which exhibits deficient or reduced α-KGDH activity and which has amplified PPC and GDH activities For the purpose of producing L-glutamic acid by fermentation using an L-glutamic acid-producing mutant of the genus Escherichia which exhibits deficient or reduced α-KGDH activity and which has amplified PPC and GDH activities, a standard culture medium containing one or more carbon sources, one or more nitrogen sources, essential and/or non-essential inorganic salts and, if necessary or desired, organic trace nutrients such as amino acids and vitamins and may be employed in accordance with standard culture methods. The carbon sources and the nitrogen sources employed in the culture medium may be any of those catabolized by the mutant employed.

The carbon sources may include saccharides and organic acids. Suitable saccharides may include glucose, glycerol, fructose, sucrose, maltose, mannose, galactose, starch hydrolysate and molasses. Suitable organic acids may include acetic acid and citric acid. Any of the carbon sources may be employed independently or in combination with other carbon sources.

The nitrogen sources may include ammonia, ammonium salts such as ammonium sulfate, ammonium carbonate, ammonium chloride, ammonium phosphate and ammonium acetate, and nitrate salts such as sodium nitrate and potassium nitrate.

The organic trace nutrients may include amino acids, vitamins, fatty acids and nucleic acids, as they are or as contained in peptone, casamino acid, yeast extract, soy protein hydrolysate and the like. In cases of using an auxotroph, the nutrient required by the auxotroph should be supplemented in the culture medium.

Suitable inorganic salts may include alkali metal and alkaline earth metal phosphate salts, other biologically acceptable magnesium salts and calcium salts, biologically acceptable iron and manganese salts, and the like.

Cultivation/fermentation is conducted (preferably with aeration) at a temperature of from 20° to 45° C. and at a pH of from 5 to 9. The pH is preferably controlled such that it is maintained in the given range (5–9). When the pH is controlled during cultivation, calcium carbonate or an alkali (such as ammonia gas) may be added to the culture medium to neutralize the acid(s) produced by the culture (which may result in lowering the pH to 5 or less). After culturing for a length of time from 10 hours to 4 days, a significant amount of L-glutamic acid is accumulated in the culture medium.

L-glutamic acid in the culture medium after cultivation may be recovered by any known method. For example, the cells may be removed from the culture. The culture medium may then be concentrated and the L-glutamic acid precipitated (e.g., by adding acid to reduce its solubility). Alternatively, the cell-free culture medium may be subjected to ion exchange chromatography to obtain the L-glutamic acid.

The present invention is further described in the following examples, which are given for illustration of the present invention, and are not intended to be limiting thereof. Additional features of the present invention will become readily apparent in the course of the following descriptions of exemplary embodiments.

EXAMPLE 1

(1) Cloning of the sucA and dihydrolipoamide succinyl transferase gene of *Escherichia coli*

The nucleotide sequences of the sucA and dihydrolipoamide succinyl transferase genes (hereinafter, the dihydrolipoamide succinyl transferase gene is referred to as the sucB gene) of *Escherichia coli* K12 are known. The known nucleotide sequences of the sucA and sucB genes are disclosed in *Euro. J. Biochem.*, Vol. *141*, pp. 351 to 374 (1984), and are also shown below as SEQ ID NO:7 in the Sequence Listing. The nucleotide sequence from the 327th through the 3128th residues corresponds to the ORF (open reading frame) of the sucA gene, while the nucleotide sequence from the 3143rd through the 4357th residues corresponds to the ORF of the sucB gene. Based on the nucleotide sequences reported, primers were synthesized (SEQ ID NOS:1–4), and the sucA and sucB genes were amplified by PCR, employing the chromosomal DNA of *Escherichia coli* W3110 as a template.

The synthetic primers used to amplify the sucA gene had the nucleotide sequences of SEQ ID NOS:1–2. Sequence ID No. 1 corresponds to the sequence consisting of the 45th through 65th base residues in the nucleotide sequence figure of the sucA gene described in *Euro. J. Biochem.*, Vol. 141, p. 354 (1984). It also corresponds to the sequence consisting of bases 45–65 of SEQ ID NO:7.

Sequence ID No. 2 corresponds to the sequence consisting of the 3173rd through 3193rd base residues in the nucleotide sequence figure of the sucB gene as shown in *Euro. J. Biochem.*, Vol. 141, p. 364 (1984). It also corresponds to the sequence consisting of bases 3173–3193 of SEQ ID NO:7.

The synthetic primers used to amplify the sucB gene had the nucleotide sequences of SEQ ID NOS:3–4. Sequence ID No. 3 corresponds to the sequence consisting of the 2179th through 2198th base residues in the nucleotide sequence figure of the sucA gene as shown in *Euro. J. Biochem.*, Vol. 141, p. 354 (1984). It also corresponds to the sequence consisting of bases 2179–2198 of SEQ ID NO:7.

Sequence ID No. 4 corresponds to the sequence consisting of the 4566th–4591st base residues in the nucleotide sequence figure of the sucB gene shown in *Euro. J. Biochem.*, Vol. 141, p. 364 (1984). It also corresponds to the sequence consisting of bases 4566–4591 of SEQ ID NO:7. The sucA gene and the sucB gene form an operon.

The chromosomal DNA of *Escherichia coli* W3110 was recovered by a standard method (Seibutsukogaku Jikkensho, ed. by Nippon Seibutsu Kogaku Kai, pp. 97 to 98, Baifukan (1992)).

PCR was carried out under standard conditions, as described on page 8 of PCR Technology (Henry Erlich, ed., Stockton Press (1989)).

Both ends of the PCR products thus produced were converted into blunt ends using T4 DNA polymerase, and were subsequently cloned into a vector pBR322 at the EcoRV site. The plasmid obtained by cloning the sucA gene into pBR322 was designated as pBR-sucA, and that constructed with the sucB gene was designated as pBR-sucB. The plasmids thus obtained were introduced into *Escherichia coli* JM109 and the transformant was cultured. Restriction maps were then constructed and compared with the restriction maps of the sucA and sucB genes reported, thereby confirming that the genes which had been cloned were the sucA and sucB genes.

As shown in FIG. 1, pBR-sucB was digested with KpnI and EcoRI to prepare a DNA fragment containing the sucB gene. pBR-sucA was digested with KpnI and EcoRI to prepare a large fragment. Both fragments were ligated using T4 DNA ligase to produce pBR-sucAB. (2) Disruption of the sucA gene on the chromosomal DNA of

*Escherichia coli* W3110

Figure 2:
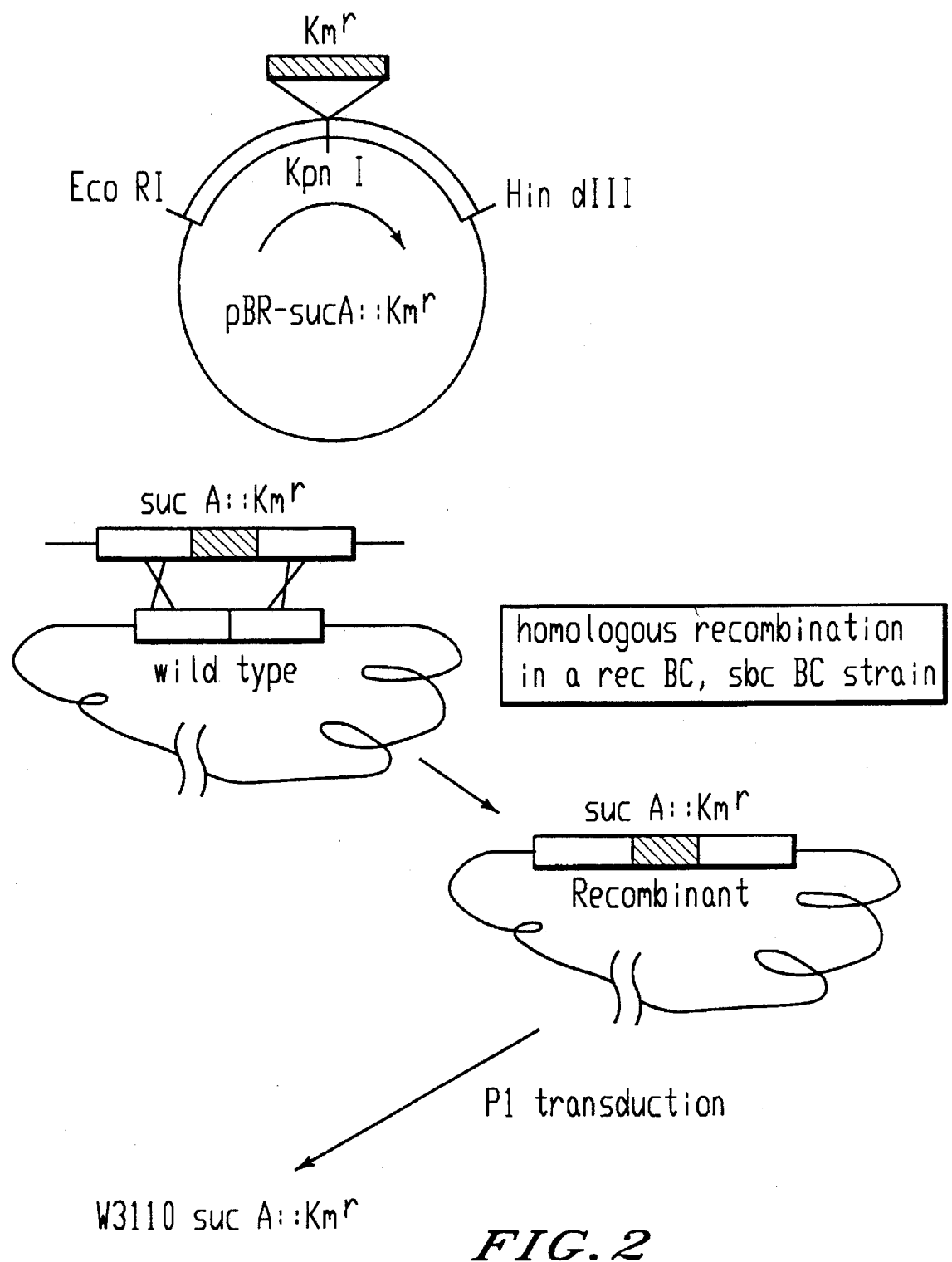
FIG. 2 shows the procedure for disrupting the sucA gene on *Escherichia coli* W3110 chromosomal DNA.

FIG. 2 outlines the disruption of the sucA gene on the chromosomal DNA of *Escherichia coli* W3110.

pBR-sucAB was digested with KpnI and T4 DNA polymerase was used to obtain blunt ends. On the other hand, pUC4K (purchased from Pharmacia) was digested with PstI to prepare a DNA fragment containing a kanamycin-resistance gene, which was converted to have blunt ends using T4 DNA polymerase. Both fragments were ligated using T4 DNA ligase to obtain pBR-sucA::Km$^r$. From this plasmid, a HindIII-EcoRI fragment containing the kanamycin-resistance gene was cut out as a linear DNA, which was used to transform *Escherichia coli* JC7623 (thr-1, ara-14, leuB6, Δ(gpt-proA)62, lacY1, tsx-23, supE44, galK2, λ$^-$ rac$^-$, sbcB15, hisG4, rfbD1, recB21, recC22, rpsL31, kdgK51, xyl-5, mtl-1, argE3, thi-1), obtained from the *Escherichia coli* Genetic Stock Center (at Yale University, USA). Strains in which the sucA gene on the chromosomal DNA was replaced with the sucA gene into which the kanamycin-resistance gene (sucA::Km$^r$) had been inserted were screened on L medium (bactotrypton 10 g/l, yeast extract 5 g/l, NaCl 5 g/, agar 15 g/l, pH 7.2), supplemented with 25 g/ml of kanamycin. Since *Escherichia coli* JC7623 possesses recB–, recC– and sbcB– genes, recombination can be achieved at a high frequency, even if the transformation is conducted using linear DNA.

From each of twelve (12) kanamycin-resistant strains thus obtained, the chromosomal DNA was prepared and digested with KpnI. By Southern hybridization using a DNA fragment containing the sucA gene as a probe, all 12 strains were confirmed to be strains in which the sucA gene on the chromosomal DNA was replaced with the sucA gene into which the kanamycin-resistance gene had been inserted. While a wild strain exhibits two bands at 5.2 Kb and 6.2 Kb due to the presence of a KpnI site in the DNA fragment containing the sucA gene, when a 2.6 Kb EcoRI-HindIII fragment containing the sucA gene of pBR-sucA was used as the probe in the Southern hybridization, strains having the sucA gene into which the kanamycin-resistance gene has been inserted exhibit only one band at 11.4 Kb due to the disruption of the KpnI site upon introduction of the kanamycin-resistance gene. The kanamycin-resistant *Escherichia coli* JC7623 (sucA::Km$^r$ ) thus obtained was then infected with P1 phage, and the phage lysate was prepared.

*Escherichia coli* W3110 was then transduced with the sucA::Km$^r$. Transduction with P1 phage was conducted by a standard method (Seibutsu-kogaku Jikkensho, Nippon Seibutsu Kogaku Kai, ed., pp. 75 to 76, Baifukan (1992)). One representative strain of the kanamycin-resistant strains isolated was designated as W3110 sucA::Km$^r$.

The α-KGDH activities of the strain W3110 sucA::Km$^r$ and *Escherichia coli* W3110 were determined according to the method described by Reed et al ("Methods in Enzymology," Vol. 13, pp. 55 (1969)). The results are shown in Table 1. No α-KGDH activity was detected in *Escherichia coli* W3110 sucA::Km$^r$. Thus, *Escherichia coli* W3110 sucA::Km$^r$ is a strain whose α-KGDH activity is deficient.

TABLE 1

|  | W3110 | W3110-sucA::Km$^r$ |
| --- | --- | --- |
| α-KGDH activity | 3.70 | Not detected |

(Unit of activity = micromoles/mg protein/min)

(3) Cloning the gdhA gene of *Escherichia coli* W3110

Similar to the cloning of the sucA and sucB genes, PCR was used to clone the gdhA gene. Based on the nucleotide sequence of the gdhA gene reported by Fernando et al, primers for PCR were synthesized. The nucleotide sequence of the gdhA gene is disclosed in Gene, Vol. 27, pp. 193 to 199 (1984), and is also shown here as SEQ ID NO:8 in the Sequence Listing. The nucleotide sequences of the primers are shown as SEQ ID NOS:5-6.

Sequence ID No. 5 corresponds to the sequence from the −191st through the −171st residues in the nucleotide sequence figure of the gdhA gene shown in Gene, Vol. 27, p.195 (1984), and it also corresponds to the sequence from the 3rd through the 23rd residues in SEQ ID NO:8. Sequence ID No. 6 corresponds to the sequence consisting of the 1687th through the 1707th residues in the nucleotide sequence figure of the gdhA gene shown in Gene, Vol. 27, p.195, (1984), and it also corresponds to the sequence consisting of the 1880th through the 1900th residues in SEQ ID NO:8.

Using the synthetic primers, the gdhA gene was amplified by PCR, employing the chromosomal DNA of *Escherichia coli* W3110 as a template. PCR products thus obtained were purified and converted to have blunt ends using T4 DNA polymerase, then ligated to pBR322 digested with EcoRV to obtain a plasmid pBRGDH.

(4) Construction of a plasmid having the ppc and gdhA genes

Figure 3:
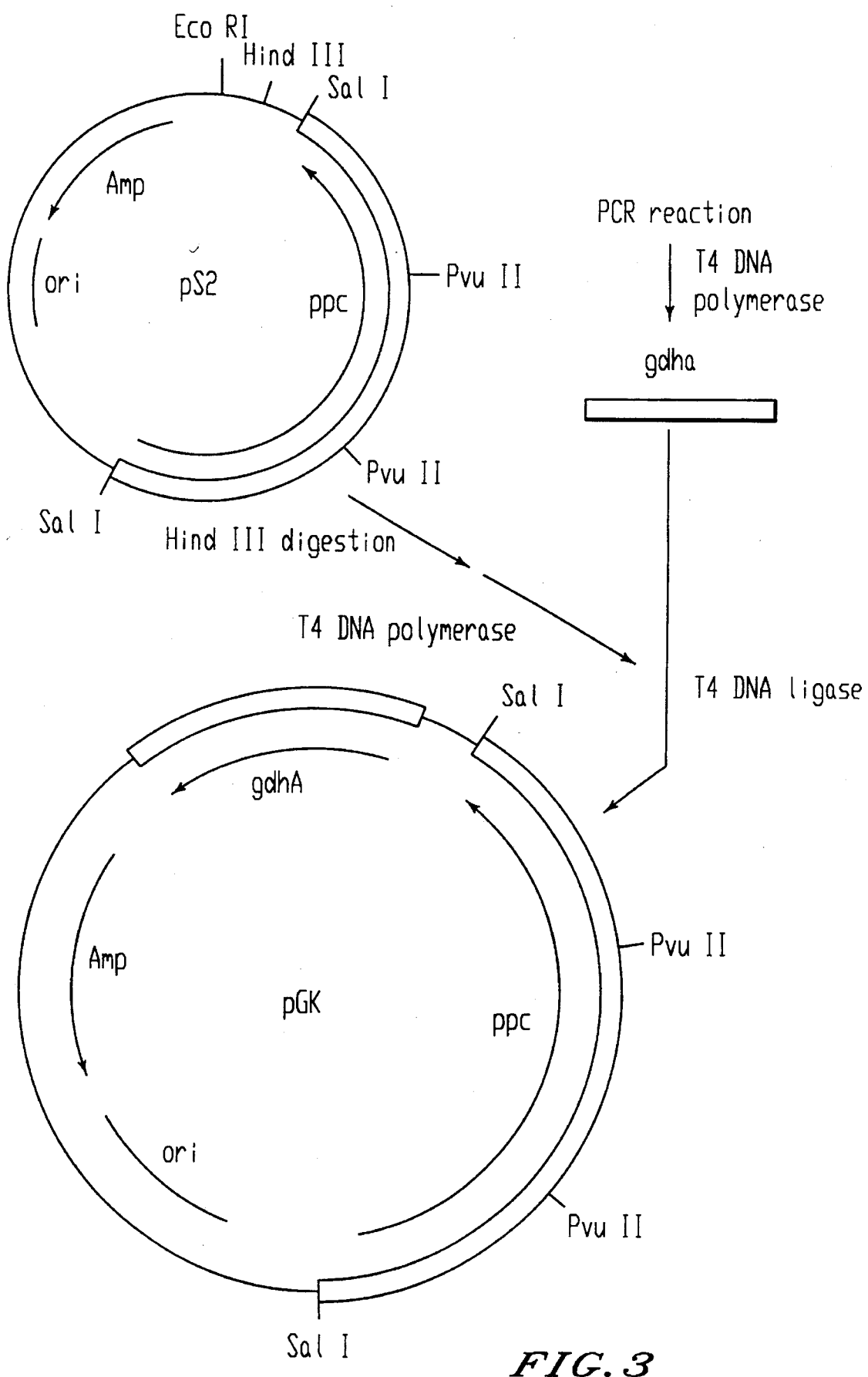
FIG. 3 shows the procedure for constructing pGK.

FIG. 3 shows the procedure for the construction of a plasmid having the ppc and gdhA genes. The plasmid pS2, in which a 4.4 Kb SalI fragment containing the entire ppc gene derived from *Escherichia coli* K-12 has been inserted into the SalI site of pBR322 (J. Biochem., Vol. 9, pp. 909 to 916 (1984)), was digested with HindIII and both ends were blunted using T4 DNA polymerase. On the other hand, a DNA fragment containing the gdhA gene synthesized by PCR was blunt-ended using T4 DNA polymerase. Subsequently, both fragments were ligated using T4 DNA ligase. The plasmid thus obtained was used to transform a GDH-deficient strain, *Escherichia coli* PA 340 (thr-1, fhuA2, leuB6, lacY1, supE44, gal-6, λ$^-$ gdh$^-$1, hisG1, rfbD1, galP63, Δ(gltB–F), rpsL19, malT1(lambdaR), yl-7mtl-2, argH1, thi-1), obtained from the *Escherichia coli* Genetic Stock Center (at Yale University, USA). An ampicillin-resistant strain which lost its glutamic acid requirement for growth was isolated. From this strain, a plasmid was prepared and the corresponding restriction map was constructed, whereby it was confirmed that the ppc and gdhA genes were present on this plasmid. This plasmid was designated as pGK.

(5) Introduction of pS2, pBRGDH and pGK into α-KGDH-deficient strain *Escherichia coli* W3100 sucA::Km$^r$, and evaluation of L-glutamic acid production by the transformants In separate procedures, the α-KGDH-deficient strain *Escherichia coli* W3100 sucA::Km$^r$ was transformed with each of pS2, pBRGDH and pGK. Each of the transformed strains was inoculated into a 500-ml shaker flask containing 20 ml of the culture medium having the composition shown in Table 2. Each of the cultures was then cultivated at 37° C.

until the glucose in the culture medium was consumed completely. The results are shown in Table 3.

TABLE 2

| Component | Concentration (g/l) |
| --- | --- |
| Glucose | 40 |
| $(NH_4)_2SO_4$ | 20 |
| $KH_2PO_4$ | 1 |
| $MgSO_4.7H_2O$ | 1 |
| $FeSO_4.7H_2O$ | 0.01 |
| $MnSO_4.5H_2O$ | 0.01 |
| Yeast extract | 2 |
| Thiamine hydrochloride | 0.01 |
| $CaCO_3$ | 50 |

TABLE 3

| Strain | Accumulated L-glutamic acid (g/l) |
| --- | --- |
| W3110 sucA::$Km^r$ | 19.2 |
| W3110 sucA::$Km^r$/pS2 | 19.9 |
| W3110 sucA::$Km^r$/pBRGDH | 2.8 |
| W3110 sucA::$Km^r$/pGK (AJ 12949) | 23.3 |

Although the transformed strain having amplified PPC activity (W3110 sucA::$Km^r$/pS2) exhibited slightly reduced growth as compared with the host strain, W3110 sucA::$Km^r$, it accumulated L-glutamic acid in an amount similar to that accumulated by the host strain. The strain having amplified GDH activity (W3110 sucA::$Km^r$/pBRGDH) exhibited quite poor growth, and the amount of the accumulated L-glutamic acid was surprisingly smaller than that accumulated by the host strain W3110 sucA::$Km^r$.

On the contrary, the transformed strain in which both of PPC and GDH activities were amplified simultaneously (W3110 sucA::$Km^r$/pGK) exhibited growth similar to that of the host strain, while also providing an increased amount of accumulated L-glutamic acid. *Escherichia coli* W3110 sucA::$Km^r$/pGK, designated as AJ 12949, was originally deposited under the accession number FERM P-14039 on Dec. 28, 1993, at the National Institute of Bioscience and Human-Technology, Agency of Industrial Science and Technology, 1–3, Higashi 1-chome, Tsukuba-shi, Ibaraki-ken 305, Japan. The deposit was converted into a deposit under the Budapest Treaty under the accession number FERM BP4881 on Nov. 11, 1994.

The host strain W3110 sucA::$Km^r$ can be obtained by curing the plasmid from the deposited strain AJ 12949 without damaging the cell. The plasmid may be lost from AJ 12949 spontaneously, or may be cured in a curing procedure (Bact. Rev., Vol. 36, p. 361 to 405 (1972)). An example of the curing procedure is as follows.

The strain AJ 12949 is inoculated in an L-broth medium (10 g/l Bactotrypton, 5 g/l yeast extract, 5 g/l NaCl, pH 7.2), and cultivated at 40° C. overnight. The culture broth is diluted appropriately and spread onto the L-medium. After incubating it at 37° C. overnight, the colonies formed are transferred to the L-medium containing 100 µg/ml of ampicillin, then ampicillin-sensitive colonies are isolated. The strain thus obtained is W3110 sucA::$Km^r$.

SUMMARY

The present method and mutant provide increased productivity of L-glutamic acid, as well as the efficient and low-cost production of L-glutamic acid.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A mutant of the genus Escherichia which produces L-glutamic acid, the α-ketoglutarate dehydrogenase activity of which is deficient or reduced, and the phosphoenol pyruvate carboxylase and glutamate dehydrogenase activities of which are amplified.

2. A method of producing L-glutamic acid, comprising culturing in a liquid culture medium the mutant of claim 1, and recovering L-glutamic acid from said liquid culture medium.

3. The method of claim 2, wherein said culturing is conducted for a length of time of from 10 hours to 4 days.

4. The method of claim 2, wherein said culturing is conducted at a temperature of from 20° to 44° C.

5. The method of claim 2, wherein said culturing is conducted at a pH of from 5 to 9, and said method further comprises adding an alkaline agent to said liquid culture medium in a manner effective to maintain said pH.

6. E. coli W3110 sucA::Km$^r$/pGK desposited under the provisions of the Budapest Treaty under the accession number FERM BP4881 on Nov. 11, 1994 at the National Institute of Bioscience and Human Technology, Agency of Industrial Science and Technology, 1-3, Higashi 1 chome, Tsukuba-shi, Ibaraki-ken 305 Japan.

* * * * *

UNITED STATES PATENT AND TRADEMARK OFFICE
CERTIFICATE OF CORRECTION

PATENT NO. : 5,573,945
DATED : November 12, 1996
INVENTOR(S) : Eiji ONO, et al.

It is certified that error appears in the above-identified patent and that said Letters Patent is hereby corrected as shown below:

Column 3, line 62, "a-ketoglutaric" should read --α-ketoglutaric--;
    line 65, "eα-KGDH" should read --α-KGDH--.

Column 7, line 29, "g/ml" should read --μg/mℓ--.

Signed and Sealed this

Second Day of December, 1997

BRUCE LEHMAN

Attest:

Attesting Officer    Commissioner of Patents and Trademarks

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="synthetic DNA"

( i x ) FEATURE:
        ( A ) NAME/KEY: misc_feature
        ( B ) LOCATION: 1..21
        ( D ) OTHER INFORMATION: /note="Primer for amplification of
            sucA gene of Escherichia coli"

( x i ) SEQUENCE DESCRIPTION: SEQ ID NO:1:

ACGCGCAAGC GTCGCATCAG G                              2 1

( 2 ) INFORMATION FOR SEQ ID NO:2:

( i ) SEQUENCE CHARACTERISTICS:

( A ) LENGTH: 21 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc ="synthetic DNA"

( i x ) FEATURE:
                ( A ) NAME/KEY: misc_feature
                ( B ) LOCATION: 1..21
                ( D ) OTHER INFORMATION: /note="Primer for amplification of
                       sucA gene of Escherichia coli"

( x i ) SEQUENCE DESCRIPTION: SEQ ID NO:2:

ATCGGCTACG AATTCAGGCA G                                                                 2 1

( 2 ) INFORMATION FOR SEQ ID NO:3:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: misc_feature
                ( B ) LOCATION: 1..20
                ( D ) OTHER INFORMATION: /note="Primer for amplification of
                       sucB gene of Escherichia coli"

( x i ) SEQUENCE DESCRIPTION: SEQ ID NO:3:

CCGGTCGCGG TACCTTCTTC                                                                   2 0

( 2 ) INFORMATION FOR SEQ ID NO:4:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: misc_feature
                ( B ) LOCATION: 1..26
                ( D ) OTHER INFORMATION: /note="Primer for amplification of
                       sucB gene of Escherichia coli"

( x i ) SEQUENCE DESCRIPTION: SEQ ID NO:4:

CGTAGACCGA ATTCTTCGTA TCGCTT                                                            2 6

( 2 ) INFORMATION FOR SEQ ID NO:5:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: misc_feature
                ( B ) LOCATION: 1..21
                ( D ) OTHER INFORMATION: /note="Primer for amplification of
                       gdhA gene of Escherichia coli"

( x i ) SEQUENCE DESCRIPTION: SEQ ID NO:5:

GGGTGGCAAA GCTTTAGCGT C                                                                 2 1

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..21
        ( D ) OTHER INFORMATION: /note="Primer for amplification of
                gdhA gene of Escherichia coli"

( x i ) SEQUENCE DESCRIPTION: SEQ ID NO:6:

```
TCGAGAAGCA TGCATTATAT A                                                        21
```

( 2 ) INFORMATION FOR SEQ ID NO:7:

( i ) SEQUENCE CHARACTERISTICS:
        ( A ) LENGTH: 4623 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Escherichia coli ( i x ) FEATURE:
        ( A ) NAME/KEY: CDS
        ( B ) LOCATION: 327..3128
        ( D ) OTHER INFORMATION: /note="Method of feature
                determination: E"

( i x ) FEATURE:
        ( A ) NAME/KEY: CDS
        ( B ) LOCATION: 3143..4357
        ( D ) OTHER INFORMATION: /note="Method of feature
                determination: E"

( x i ) SEQUENCE DESCRIPTION: SEQ ID NO:7:

```
TCGATGTTGT  TGCAACGTAA  TGCGTAAACC  GTAGGCCTGA  TAAGACGCGC  AAGCGTCGCA         60

TCAGGCAACC  AGTGCCGGAT  GCGCGTGAAC  GCCTTATCCG  GCCTACAAGT  CATTACCCGT        120

AGGCCTGATA  AGCGCAGCGC  ATCAGGCGTA  ACAAAGAAAT  GCAGGAAATC  TTTAAAAACT        180

GCCCCTGACA  CTAAGACAGT  TTTTAAAGGT  TCCTTCGCGA  GCCACTACGT  AGACAAGAGC        240

TCGCAAGTGA  ACCCCGGCAC  GCACATCACT  GTGCGTGGTA  GTATCCACGG  CGAAGTAAGC        300

ATAAAAAAGA  TGCTTAAGGG  ATCACG ATG  CAG  AAC  AGC  GCT  TTG  AAA  GCC  TGG    353
                                   Met  Gln  Asn  Ser  Ala  Leu  Lys  Ala  Trp
                                    1                    5

TTG  GAC  TCT  TCT  TAC  CTC  TCT  GGC  GCA  AAC  CAG  AGC  TGG  ATA  GAA  CAG    401
Leu  Asp  Ser  Ser  Tyr  Leu  Ser  Gly  Ala  Asn  Gln  Ser  Trp  Ile  Glu  Gln
 10                 15                      20                      25

CTC  TAT  GAA  GAC  TTC  TTA  ACC  GAT  CCT  GAC  TCG  GTT  GAC  GCT  AAC  TGG    449
Leu  Tyr  Glu  Asp  Phe  Leu  Thr  Asp  Pro  Asp  Ser  Val  Asp  Ala  Asn  Trp
                     30                  35                      40

CGT  TCG  ACG  TTC  CAG  CAG  TTA  CCT  GGT  ACG  GGA  GTC  AAA  CCG  GAT  CAA    497
Arg  Ser  Thr  Phe  Gln  Gln  Leu  Pro  Gly  Thr  Gly  Val  Lys  Pro  Asp  Gln
              45                      50                      55

TTC  CAC  TCT  CAA  ACG  CGT  GAA  TAT  TTC  CGC  CGC  CTG  GCG  AAA  GAC  GCT    545
Phe  His  Ser  Gln  Thr  Arg  Glu  Tyr  Phe  Arg  Arg  Leu  Ala  Lys  Asp  Ala
         60                      65                      70
```

| | | | | | | | | | | | | | | | | |
|---|---|---|---|---|---|---|---|---|---|---|---|---|---|---|---|---|
| TCA | CGT | TAC | TCT | TCA | ACG | ATC | TCC | GAC | CCT | GAC | ACC | AAT | GTG | AAG | CAG | 593 |
| Ser | Arg | Tyr | Ser | Ser | Thr | Ile | Ser | Asp | Pro | Asp | Thr | Asn | Val | Lys | Gln | |
| | 75 | | | | 80 | | | | | 85 | | | | | | |
| GTT | AAA | GTC | CTG | CAG | CTC | ATT | AAC | GCA | TAC | CGC | TTC | CGT | GGT | CAC | CAG | 641 |
| Val | Lys | Val | Leu | Gln | Leu | Ile | Asn | Ala | Tyr | Arg | Phe | Arg | Gly | His | Gln | |
| 90 | | | | | 95 | | | | | 100 | | | | | 105 | |
| CAT | GCG | AAT | CTC | GAT | CCG | CTG | GGA | CTG | TGG | CAG | CAA | GAT | AAA | GTG | GCC | 689 |
| His | Ala | Asn | Leu | Asp | Pro | Leu | Gly | Leu | Trp | Gln | Gln | Asp | Lys | Val | Ala | |
| | | | | 110 | | | | | 115 | | | | | 120 | | |
| GAT | CTG | GAT | CCG | TCT | TTC | CAC | GAT | CTG | ACC | GAA | GCA | GAC | TTC | CAG | GAG | 737 |
| Asp | Leu | Asp | Pro | Ser | Phe | His | Asp | Leu | Thr | Glu | Ala | Asp | Phe | Gln | Glu | |
| | | | 125 | | | | | 130 | | | | | 135 | | | |
| ACC | TTC | AAC | GTC | GGT | TCA | TTT | GCC | AGC | GGC | AAA | GAA | ACC | ATG | AAA | CTC | 785 |
| Thr | Phe | Asn | Val | Gly | Ser | Phe | Ala | Ser | Gly | Lys | Glu | Thr | Met | Lys | Leu | |
| | | 140 | | | | | 145 | | | | | 150 | | | | |
| GGC | GAG | CTG | CTG | GAA | GCC | CTC | AAG | CAA | ACC | TAC | TGC | GGC | CCG | ATT | GGT | 833 |
| Gly | Glu | Leu | Leu | Glu | Ala | Leu | Lys | Gln | Thr | Tyr | Cys | Gly | Pro | Ile | Gly | |
| | 155 | | | | | 160 | | | | | 165 | | | | | |
| GCC | GAG | TAT | ATG | CAC | ATT | ACC | AGC | ACC | GAA | GAA | AAA | CGC | TGG | ATC | CAA | 881 |
| Ala | Glu | Tyr | Met | His | Ile | Thr | Ser | Thr | Glu | Glu | Lys | Arg | Trp | Ile | Gln | |
| 170 | | | | | 175 | | | | | 180 | | | | | 185 | |
| CAG | CGT | ATC | GAG | TCT | GGT | CGC | GCG | ACT | TTC | AAT | AGC | GAA | GAG | AAA | AAA | 929 |
| Gln | Arg | Ile | Glu | Ser | Gly | Arg | Ala | Thr | Phe | Asn | Ser | Glu | Glu | Lys | Lys | |
| | | | | 190 | | | | | 195 | | | | | 200 | | |
| CGC | TTC | TTA | AGC | GAA | CTG | ACC | GCC | GCT | GAA | GGT | CTT | GAA | CGT | TAC | CTC | 977 |
| Arg | Phe | Leu | Ser | Glu | Leu | Thr | Ala | Ala | Glu | Gly | Leu | Glu | Arg | Tyr | Leu | |
| | | | 205 | | | | | 210 | | | | | 215 | | | |
| GGC | GCA | AAA | TTC | CCT | GGC | GCA | AAA | CGC | TTC | TCG | CTG | GAA | GGC | GGT | GAC | 1025 |
| Gly | Ala | Lys | Phe | Pro | Gly | Ala | Lys | Arg | Phe | Ser | Leu | Glu | Gly | Gly | Asp | |
| | | 220 | | | | | 225 | | | | | 230 | | | | |
| GCG | TTA | ATC | CCG | ATG | CTT | AAA | GAG | ATG | ATC | CGC | CAC | GCT | GGC | AAC | AGC | 1073 |
| Ala | Leu | Ile | Pro | Met | Leu | Lys | Glu | Met | Ile | Arg | His | Ala | Gly | Asn | Ser | |
| | 235 | | | | | 240 | | | | | 245 | | | | | |
| GGC | ACC | CGC | GAA | GTG | GTT | CTC | GGG | ATG | GCG | CAC | CGT | GGT | CGT | CTG | AAC | 1121 |
| Gly | Thr | Arg | Glu | Val | Val | Leu | Gly | Met | Ala | His | Arg | Gly | Arg | Leu | Asn | |
| 250 | | | | | 255 | | | | | 260 | | | | | 265 | |
| GTG | CTG | GTG | AAC | GTG | CTG | GGT | AAA | AAA | CCG | CAA | GAC | TTG | TTC | GAC | GAG | 1169 |
| Val | Leu | Val | Asn | Val | Leu | Gly | Lys | Lys | Pro | Gln | Asp | Leu | Phe | Asp | Glu | |
| | | | | 270 | | | | | 275 | | | | | 280 | | |
| TTC | GCC | GGT | AAA | CAT | AAA | GAA | CAC | CTC | GGC | ACG | GGT | GAC | GTG | AAA | TAC | 1217 |
| Phe | Ala | Gly | Lys | His | Lys | Glu | His | Leu | Gly | Thr | Gly | Asp | Val | Lys | Tyr | |
| | | | 285 | | | | | 290 | | | | | 295 | | | |
| CAC | ATG | GGC | TTC | TCG | TCT | GAC | TTC | CAG | ACC | GAT | GGC | GGC | CTG | GTG | CAC | 1265 |
| His | Met | Gly | Phe | Ser | Ser | Asp | Phe | Gln | Thr | Asp | Gly | Gly | Leu | Val | His | |
| | | 300 | | | | | 305 | | | | | 310 | | | | |
| CTG | GCG | CTG | GCG | TTT | AAC | CCG | TCT | CAC | CTT | GAG | ATT | GTA | AGC | CCG | GTA | 1313 |
| Leu | Ala | Leu | Ala | Phe | Asn | Pro | Ser | His | Leu | Glu | Ile | Val | Ser | Pro | Val | |
| | 315 | | | | | 320 | | | | | 325 | | | | | |
| GTT | ATC | GGT | TCT | GTT | CGT | GCC | CGT | CTG | GAC | AGA | CTT | GAT | GAG | CCG | AGC | 1361 |
| Val | Ile | Gly | Ser | Val | Arg | Ala | Arg | Leu | Asp | Arg | Leu | Asp | Glu | Pro | Ser | |
| 330 | | | | | 335 | | | | | 340 | | | | | 345 | |
| AGC | AAC | AAA | GTG | CTG | CCA | ATC | ACC | ATC | CAC | GGT | GAC | GCC | GCA | GTG | ACC | 1409 |
| Ser | Asn | Lys | Val | Leu | Pro | Ile | Thr | Ile | His | Gly | Asp | Ala | Ala | Val | Thr | |
| | | | | 350 | | | | | 355 | | | | | 360 | | |
| GGG | CAG | GGC | GTG | GTT | CAG | GAA | ACC | CTG | AAC | ATG | TCG | AAA | GCG | CGT | GGT | 1457 |
| Gly | Gln | Gly | Val | Val | Gln | Glu | Thr | Leu | Asn | Met | Ser | Lys | Ala | Arg | Gly | |
| | | | | 365 | | | | | 370 | | | | | 375 | | |
| TAT | GAA | GTT | GGC | GGT | ACG | GTA | CGT | ATC | GTT | ATC | AAC | AAC | CAG | GTT | GGT | 1505 |
| Tyr | Glu | Val | Gly | Gly | Thr | Val | Arg | Ile | Val | Ile | Asn | Asn | Gln | Val | Gly | |
| | | | 380 | | | | | 385 | | | | | 390 | | | |

| | | | | | | | | | | | | | | | | |
|---|---|---|---|---|---|---|---|---|---|---|---|---|---|---|---|---|
| TTC | ACC | ACC | TCT | AAT | CCG | CTG | GAT | GCC | CGT | TCT | ACG | CCG | TAC | TGT | ACT | 1553 |
| Phe | Thr | Thr | Ser | Asn | Pro | Leu | Asp | Ala | Arg | Ser | Thr | Pro | Tyr | Cys | Thr | |
| 395 | | | | | 400 | | | | | 405 | | | | | | |
| GAT | ATC | GGT | AAG | ATG | GTT | CAG | GCC | CCG | ATT | TTC | CAC | GTT | AAC | GCG | GAC | 1601 |
| Asp | Ile | Gly | Lys | Met | Val | Gln | Ala | Pro | Ile | Phe | His | Val | Asn | Ala | Asp | |
| 410 | | | | | 415 | | | | | 420 | | | | | 425 | |
| GAT | CCG | GAA | GCC | GTT | GCC | TTT | GTG | ACC | CGT | CTG | GCG | CTC | GAT | TTC | CGT | 1649 |
| Asp | Pro | Glu | Ala | Val | Ala | Phe | Val | Thr | Arg | Leu | Ala | Leu | Asp | Phe | Arg | |
| | | | | 430 | | | | | 435 | | | | | 440 | | |
| AAC | ACC | TTT | AAA | CGT | GAT | GTC | TTC | ATC | GAC | CTG | GTG | TCG | TAC | CGC | CGT | 1697 |
| Asn | Thr | Phe | Lys | Arg | Asp | Val | Phe | Ile | Asp | Leu | Val | Ser | Tyr | Arg | Arg | |
| | | | 445 | | | | | 450 | | | | | 455 | | | |
| CAC | GGC | CAC | AAC | GAA | GCC | GAC | GAG | CCG | AGC | GCA | ACC | CAG | CCG | CTG | ATG | 1745 |
| His | Gly | His | Asn | Glu | Ala | Asp | Glu | Pro | Ser | Ala | Thr | Gln | Pro | Leu | Met | |
| | | 460 | | | | | 465 | | | | | 470 | | | | |
| TAT | CAG | AAA | ATC | AAA | AAA | CAT | CCG | ACA | CCG | CGC | AAA | ATC | TAC | GCT | GAC | 1793 |
| Tyr | Gln | Lys | Ile | Lys | Lys | His | Pro | Thr | Pro | Arg | Lys | Ile | Tyr | Ala | Asp | |
| | 475 | | | | | 480 | | | | | 485 | | | | | |
| AAG | CTG | GAG | CAG | GAA | AAA | GTG | GCG | ACG | CTG | GAA | GAT | GCC | ACC | GAG | ATG | 1841 |
| Lys | Leu | Glu | Gln | Glu | Lys | Val | Ala | Thr | Leu | Glu | Asp | Ala | Thr | Glu | Met | |
| 490 | | | | | 495 | | | | | 500 | | | | | 505 | |
| GTT | AAC | CTG | TAC | CGC | GAT | GCG | CTG | GAT | GCT | GGC | GAT | TGC | GTA | GTG | GCA | 1889 |
| Val | Asn | Leu | Tyr | Arg | Asp | Ala | Leu | Asp | Ala | Gly | Asp | Cys | Val | Val | Ala | |
| | | | | 510 | | | | | 515 | | | | | 520 | | |
| GAG | TGG | CGT | CCG | ATG | AAC | ATG | CAC | TCT | TTC | ACC | TGG | TCG | CCG | TAC | CTC | 1937 |
| Glu | Trp | Arg | Pro | Met | Asn | Met | His | Ser | Phe | Thr | Trp | Ser | Pro | Tyr | Leu | |
| | | | 525 | | | | | 530 | | | | | 535 | | | |
| AAC | CAC | GAA | TGG | GAC | GAA | GAG | TAC | CCG | AAC | AAA | GTT | GAG | ATG | AAG | CGC | 1985 |
| Asn | His | Glu | Trp | Asp | Glu | Glu | Tyr | Pro | Asn | Lys | Val | Glu | Met | Lys | Arg | |
| | | 540 | | | | | 545 | | | | | 550 | | | | |
| CTG | CAG | GAG | CTG | GCG | AAA | CGC | ATC | AGC | ACG | GTG | CCG | GAA | GCA | GTT | GAA | 2033 |
| Leu | Gln | Glu | Leu | Ala | Lys | Arg | Ile | Ser | Thr | Val | Pro | Glu | Ala | Val | Glu | |
| | 555 | | | | | 560 | | | | | 565 | | | | | |
| ATG | CAG | TCT | CGC | GTT | GCC | AAG | ATT | TAT | GGC | GAT | CGC | CAG | GCG | ATG | GCT | 2081 |
| Met | Gln | Ser | Arg | Val | Ala | Lys | Ile | Tyr | Gly | Asp | Arg | Gln | Ala | Met | Ala | |
| 570 | | | | | 575 | | | | | 580 | | | | | 585 | |
| GCC | GGT | GAG | AAA | CTG | TTC | GAC | TGG | GGC | GGT | GCG | GAA | AAC | CTC | GCT | TAC | 2129 |
| Ala | Gly | Glu | Lys | Leu | Phe | Asp | Trp | Gly | Gly | Ala | Glu | Asn | Leu | Ala | Tyr | |
| | | | | 590 | | | | | 595 | | | | | 600 | | |
| GCC | ACG | CTG | GTT | GAT | GAA | GGC | ATT | CCG | GTT | CGC | CTG | TCG | GGT | GAA | GAC | 2177 |
| Ala | Thr | Leu | Val | Asp | Glu | Gly | Ile | Pro | Val | Arg | Leu | Ser | Gly | Glu | Asp | |
| | | | 605 | | | | | 610 | | | | | 615 | | | |
| TCC | GGT | CGC | GGT | ACC | TTC | TTC | CAC | CGC | CAC | GCG | GTG | ATC | CAC | AAC | CAG | 2225 |
| Ser | Gly | Arg | Gly | Thr | Phe | Phe | His | Arg | His | Ala | Val | Ile | His | Asn | Gln | |
| | | 620 | | | | | 625 | | | | | 630 | | | | |
| TCT | AAC | GGT | TCC | ACT | TAC | ACG | CCG | CTG | CAA | CAT | ATC | CAT | AAC | GGG | CAG | 2273 |
| Ser | Asn | Gly | Ser | Thr | Tyr | Thr | Pro | Leu | Gln | His | Ile | His | Asn | Gly | Gln | |
| | 635 | | | | | 640 | | | | | 645 | | | | | |
| GGC | GCG | TTC | CGT | GTC | TGG | GAC | TCC | GTA | CTG | TCT | GAA | GAA | GCA | GTG | CTG | 2321 |
| Gly | Ala | Phe | Arg | Val | Trp | Asp | Ser | Val | Leu | Ser | Glu | Glu | Ala | Val | Leu | |
| 650 | | | | | 655 | | | | | 660 | | | | | 665 | |
| GCG | TTT | GAA | TAT | GGT | TAT | GCC | ACC | GCA | GAA | CCA | CGC | ACT | CTG | ACC | ATC | 2369 |
| Ala | Phe | Glu | Tyr | Gly | Tyr | Ala | Thr | Ala | Glu | Pro | Arg | Thr | Leu | Thr | Ile | |
| | | | | 670 | | | | | 675 | | | | | 680 | | |
| TGG | GAA | GCG | CAG | TTC | GGT | GAC | TTC | CCC | AAC | GGT | GCG | CAG | GTG | GTT | ATC | 2417 |
| Trp | Glu | Ala | Gln | Phe | Gly | Asp | Phe | Pro | Asn | Gly | Ala | Gln | Val | Val | Ile | |
| | | | 685 | | | | | 690 | | | | | 695 | | | |
| GAC | CAG | TTC | ATC | TCC | TCT | GGC | GAA | CAG | AAA | TGG | GGC | CGG | ATG | TGT | GGT | 2465 |
| Asp | Gln | Phe | Ile | Ser | Ser | Gly | Glu | Gln | Lys | Trp | Gly | Arg | Met | Cys | Gly | |
| | | 700 | | | | | 705 | | | | | 710 | | | | |

| | | | | | | | | | | | | | | | | |
|---|---|---|---|---|---|---|---|---|---|---|---|---|---|---|---|---|
| CTG | GTG | ATG | TTG | CTG | CCG | CAC | GGT | TAC | GAA | GGG | CAG | GGG | CCG | GAG | CAC | 2513 |
| Leu | Val | Met | Leu | Leu | Pro | His | Gly | Tyr | Glu | Gly | Gln | Gly | Pro | Glu | His | |
| 715 | | | | | 720 | | | | | 725 | | | | | | |
| TCC | TCC | GCG | CGT | CTG | GAA | CGT | TAT | CTG | CAA | CTT | TGT | GCT | GAG | CAA | AAC | 2561 |
| Ser | Ser | Ala | Arg | Leu | Glu | Arg | Tyr | Leu | Gln | Leu | Cys | Ala | Glu | Gln | Asn | |
| 730 | | | | | 735 | | | | | 740 | | | | | 745 | |
| ATG | CAG | GTT | TGC | GTA | CCG | TCT | ACC | CCG | GCA | CAG | GTT | TAC | CAC | ATG | CTG | 2609 |
| Met | Gln | Val | Cys | Val | Pro | Ser | Thr | Pro | Ala | Gln | Val | Tyr | His | Met | Leu | |
| | | | | 750 | | | | | 755 | | | | | 760 | | |
| CGT | CGT | CAG | GCG | CTG | CGC | GGG | ATG | CGT | CGT | CCG | CTG | GTC | GTG | ATG | TCG | 2657 |
| Arg | Arg | Gln | Ala | Leu | Arg | Gly | Met | Arg | Arg | Pro | Leu | Val | Val | Met | Ser | |
| | | | | 765 | | | | | 770 | | | | | 775 | | |
| CCG | AAA | TCC | CTG | CTG | CGT | CAT | CCG | CTG | GCG | GTT | TCC | AGC | CTC | GAA | GAA | 2705 |
| Pro | Lys | Ser | Leu | Leu | Arg | His | Pro | Leu | Ala | Val | Ser | Ser | Leu | Glu | Glu | |
| | | | | 780 | | | | | 785 | | | | | 790 | | |
| CTG | GCG | AAC | GGC | ACC | TTC | CTG | CCA | GCC | ATC | GGT | GAA | ATC | GAC | GAG | CTT | 2753 |
| Leu | Ala | Asn | Gly | Thr | Phe | Leu | Pro | Ala | Ile | Gly | Glu | Ile | Asp | Glu | Leu | |
| | | | | 795 | | | | | 800 | | | | | 805 | | |
| GAT | CCG | AAG | GGC | GTG | AAG | CGC | GTA | GTG | ATG | TGT | TCT | GGT | AAG | GTT | TAT | 2801 |
| Asp | Pro | Lys | Gly | Val | Lys | Arg | Val | Val | Met | Cys | Ser | Gly | Lys | Val | Tyr | |
| 810 | | | | | 815 | | | | | 820 | | | | | 825 | |
| TAC | GAC | CTG | CTG | GAA | CAG | CGT | CGT | AAG | AAC | AAT | CAA | CAC | GAT | GTC | GCC | 2849 |
| Tyr | Asp | Leu | Leu | Glu | Gln | Arg | Arg | Lys | Asn | Asn | Gln | His | Asp | Val | Ala | |
| | | | | 830 | | | | | 835 | | | | | 840 | | |
| ATT | GTG | CGT | ATC | GAG | CAA | CTC | TAC | CCG | TTC | CCG | CAT | AAA | GCG | ATG | CAG | 2897 |
| Ile | Val | Arg | Ile | Glu | Gln | Leu | Tyr | Pro | Phe | Pro | His | Lys | Ala | Met | Gln | |
| | | | 845 | | | | | 850 | | | | | 855 | | | |
| GAA | GTG | TTG | CAG | CAG | TTT | GCT | CAC | GTC | AAG | GAT | TTT | GTC | TGG | TGC | CAG | 2945 |
| Glu | Val | Leu | Gln | Gln | Phe | Ala | His | Val | Lys | Asp | Phe | Val | Trp | Cys | Gln | |
| | | | 860 | | | | | 865 | | | | | 870 | | | |
| GAA | GAG | CCG | CTC | AAC | CAG | GGC | GCA | TGG | TAC | TGC | AGC | CAG | CAT | CAT | TTC | 2993 |
| Glu | Glu | Pro | Leu | Asn | Gln | Gly | Ala | Trp | Tyr | Cys | Ser | Gln | His | His | Phe | |
| 875 | | | | | 880 | | | | | 885 | | | | | | |
| CGT | GAA | GTG | ATT | CCG | TTT | GGG | GCT | TCT | CTG | CGT | TAT | GCA | GGC | CGC | CCG | 3041 |
| Arg | Glu | Val | Ile | Pro | Phe | Gly | Ala | Ser | Leu | Arg | Tyr | Ala | Gly | Arg | Pro | |
| 890 | | | | | 895 | | | | | 900 | | | | | 905 | |
| GCC | TCC | GCC | TCT | CCG | GCG | GTA | GGG | TAT | ATG | TCC | GTT | CAC | CAG | AAA | CAG | 3089 |
| Ala | Ser | Ala | Ser | Pro | Ala | Val | Gly | Tyr | Met | Ser | Val | His | Gln | Lys | Gln | |
| | | | | 910 | | | | | 915 | | | | | 920 | | |
| CAA | CAA | GAT | CTG | GTT | AAT | GAC | GCG | CTG | AAC | GTC | GAA | TAA | ATAAAGGATA | | | 3138 |
| Gln | Gln | Asp | Leu | Val | Asn | Asp | Ala | Leu | Asn | Val | Glu | * | | | | |
| | | | 925 | | | | | 930 | | | | | | | | |
| CACA | ATG | AGT | AGC | GTA | GAT | ATT | CTG | GTC | CCT | GAC | CTG | CCT | GAA | TCC | GTA | 3187 |
| | Met | Ser | Ser | Val | Asp | Ile | Leu | Val | Pro | Asp | Leu | Pro | Glu | Ser | Val | |
| | 1 | | | | 5 | | | | | 10 | | | | | 15 | |
| GCC | GAT | GCC | ACC | GTC | GCA | ACC | TGG | CAT | AAA | AAA | CCC | GGC | GAC | GCA | GTC | 3235 |
| Ala | Asp | Ala | Thr | Val | Ala | Thr | Trp | His | Lys | Lys | Pro | Gly | Asp | Ala | Val | |
| | | | | 20 | | | | | 25 | | | | | 30 | | |
| GTA | CGT | GAT | GAA | GTG | CTG | GTA | GAA | ATC | GAA | ACT | GAC | AAA | GTG | GTA | CTG | 3283 |
| Val | Arg | Asp | Glu | Val | Leu | Val | Glu | Ile | Glu | Thr | Asp | Lys | Val | Val | Leu | |
| | | | 35 | | | | | 40 | | | | | 45 | | | |
| GAA | GTA | CCG | GCA | TCA | GCA | GAC | GGC | ATT | CTG | GAT | GCG | GTT | CTG | GAA | GAT | 3331 |
| Glu | Val | Pro | Ala | Ser | Ala | Asp | Gly | Ile | Leu | Asp | Ala | Val | Leu | Glu | Asp | |
| | | 50 | | | | | 55 | | | | | 60 | | | | |
| GAA | GGT | ACA | ACG | GTA | ACG | TCT | CGT | CAG | ATC | CTT | GGT | CGC | CTG | CGT | GAA | 3379 |
| Glu | Gly | Thr | Thr | Val | Thr | Ser | Arg | Gln | Ile | Leu | Gly | Arg | Leu | Arg | Glu | |
| | | 65 | | | | | 70 | | | | | 75 | | | | |
| GGC | AAC | AGC | GCC | GGT | AAA | GAA | ACC | AGC | GCC | AAA | TCT | GAA | GAG | AAA | GCG | 3427 |
| Gly | Asn | Ser | Ala | Gly | Lys | Glu | Thr | Ser | Ala | Lys | Ser | Glu | Glu | Lys | Ala | |
| 80 | | | | | 85 | | | | | 90 | | | | | 95 | |

| | | | | | | | | | | | | | | | | |
|---|---|---|---|---|---|---|---|---|---|---|---|---|---|---|---|---|
| TCC | ACT | CCG | GCG | CAA | CGC | CAG | CAG | GCG | TCT | CTG | GAA | GAG | CAA | AAC | AAC | 3475 |
| Ser | Thr | Pro | Ala 100 | Gln | Arg | Gln | Gln | Ala 105 | Ser | Leu | Glu | Glu | Gln 110 | Asn | Asn | |
| GAT | GCG | TTA | AGC | CCG | GCG | ATC | CGT | CGC | CTG | CTG | GCT | GAA | CAC | AAT | CTC | 3523 |
| Asp | Ala | Leu | Ser 115 | Pro | Ala | Ile | Arg | Arg 120 | Leu | Leu | Ala | Glu | His 125 | Asn | Leu | |
| GAC | GCC | AGC | GCC | ATT | AAA | GGC | ACC | GGT | GTG | GGT | GGT | CGT | CTG | ACT | CGT | 3571 |
| Asp | Ala | Ser 130 | Ala | Ile | Lys | Gly | Thr 135 | Gly | Val | Gly | Gly | Arg 140 | Leu | Thr | Arg | |
| GAA | GAT | GTG | GAA | AAA | CAT | CTG | GCG | AAA | GCC | CCG | GCG | AAA | GAG | TCT | GCT | 3619 |
| Glu | Asp 145 | Val | Glu | Lys | His 150 | Leu | Ala | Lys | Ala 155 | Pro | Ala | Lys | Glu | Ser 160 | Ala | |
| CCG | GCA | GCG | GCT | GCT | CCG | GCG | GCG | CAA | CCG | GCT | CTG | GCT | GCA | CGT | AGT | 3667 |
| Pro 160 | Ala | Ala | Ala | Ala | Pro 165 | Ala | Ala | Gln | Pro 170 | Ala | Leu | Ala | Ala | Arg 175 | Ser | |
| GAA | AAA | CGT | GTC | CCG | ATG | ACT | CGC | CTG | CGT | AAG | CGT | GTG | GCA | GAG | CGT | 3715 |
| Glu | Lys | Arg | Val | Pro 180 | Met | Thr | Arg | Leu | Arg 185 | Lys | Arg | Val | Ala | Glu 190 | Arg | |
| CTG | CTG | GAA | GCG | AAA | AAC | TCC | ACC | GCC | ATG | CTG | ACC | ACG | TTC | AAC | GAA | 3763 |
| Leu | Leu | Glu | Ala 195 | Lys | Asn | Ser | Thr | Ala 200 | Met | Leu | Thr | Thr | Phe 205 | Asn | Glu | |
| GTC | AAC | ATG | AAG | CCG | ATT | ATG | GAT | CTG | CGT | AAG | CAG | TAC | GGT | GAA | GCG | 3811 |
| Val | Asn | Met 210 | Lys | Pro | Ile | Met | Asp 215 | Leu | Arg | Lys | Gln | Tyr 220 | Gly | Glu | Ala | |
| TTT | GAA | AAA | CGC | CAC | GGC | ATC | CGT | CTG | GGC | TTT | ATG | TCC | TTC | TAC | GTG | 3859 |
| Phe | Glu | Lys 225 | Arg | His | Gly | Ile | Arg 230 | Leu | Gly | Phe | Met | Ser 235 | Phe | Tyr | Val | |
| AAA | GCG | GTG | GTT | GAA | GCC | CTG | AAA | CGT | TAC | CCG | GAA | GTG | AAC | GCT | TCT | 3907 |
| Lys 240 | Ala | Val | Val | Glu | Ala 245 | Leu | Lys | Arg | Tyr | Pro 250 | Glu | Val | Asn | Ala | Ser 255 | |
| ATC | GAC | GGC | GAT | GAC | GTG | GTT | TAC | CAC | AAC | TAT | TTC | GAC | GTC | AGC | ATG | 3955 |
| Ile | Asp | Gly | Asp | Asp 260 | Val | Val | Tyr | His | Asn 265 | Tyr | Phe | Asp | Val | Ser 270 | Met | |
| GCG | GTT | TCT | ACG | CCG | CGC | GGC | CTG | GTG | ACG | CCG | GTT | CTG | CGT | GAT | GTC | 4003 |
| Ala | Val | Ser | Thr 275 | Pro | Arg | Gly | Leu | Val 280 | Thr | Pro | Val | Leu | Arg 285 | Asp | Val | |
| GAT | ACC | CTC | GGC | ATG | GCA | GAC | ATC | GAG | AAG | AAA | ATC | AAA | GAG | CTG | GCA | 4051 |
| Asp | Thr | Leu 290 | Gly | Met | Ala | Asp | Ile 295 | Glu | Lys | Lys | Ile | Lys 300 | Glu | Leu | Ala | |
| GTC | AAA | GGC | CGT | GAC | GGC | AAG | CTG | ACC | GTT | GAA | GAT | CTG | ACC | GGT | GGT | 4099 |
| Val | Lys 305 | Gly | Arg | Asp | Gly | Lys 310 | Leu | Thr | Val | Glu | Asp 315 | Leu | Thr | Gly | Gly | |
| AAC | TTC | ACC | ATC | ACC | AAC | GGT | GGT | GTG | TTC | GGT | TCC | CTG | ATG | TCT | ACG | 4147 |
| Asn 320 | Phe | Thr | Ile | Thr | Asn 325 | Gly | Gly | Val | Phe | Gly 330 | Ser | Leu | Met | Ser | Thr 335 | |
| CCG | ATC | ATC | AAC | CCG | CCG | CAG | AGC | GCA | ATT | CTG | GGT | ATG | CAC | GCT | ATC | 4195 |
| Pro | Ile | Ile | Asn | Pro 340 | Pro | Gln | Ser | Ala | Ile 345 | Leu | Gly | Met | His | Ala 350 | Ile | |
| AAA | GAT | CGT | CCG | ATG | GCG | GTG | AAT | GGT | CAG | GTT | GAG | ATC | CTG | CCG | ATG | 4243 |
| Lys | Asp | Arg | Pro 355 | Met | Ala | Val | Asn | Gly 360 | Gln | Val | Glu | Ile | Leu 365 | Pro | Met | |
| ATG | TAC | CTG | GCG | CTG | TCC | TAC | GAT | CAC | CGT | CTG | ATC | GAT | GGT | CGC | GAA | 4291 |
| Met | Tyr | Leu | Ala 370 | Leu | Ser | Tyr | Asp | His 375 | Arg | Leu | Ile | Asp | Gly 380 | Arg | Glu | |
| TCC | GTG | GGC | TTC | CTG | GTA | ACG | ATC | AAA | GAG | TTG | CTG | GAA | GAT | CCG | ACG | 4339 |
| Ser | Val 385 | Gly | Phe | Leu | Val | Thr 390 | Ile | Lys | Glu | Leu | Leu 395 | Glu | Asp | Pro | Thr | |
| CGT | CTG | CTG | CTG | GAC | GTG | TAGTAGTTTA | AGTTTCACCT | GCACTGTAGA | | | | | | | | 4387 |
| Arg 400 | Leu | Leu | Leu | Asp | Val 405 | | | | | | | | | | | |

| | | | | | |
|---|---|---|---|---|---|
| CCGGATAAGG | CATTATCGCC | TTCTCCGGCA | ATTGAAGCCT | GATGCGACGC | TGACGCGTCT | 4447 |
| TATCAGGCCT | ACGGGACCAC | CAATGTAGGT | CGGATAAGGC | GCAACGCCGC | ATCCGACAAG | 4507 |
| CGATGCCTGA | TGTGACGTTT | AACGTGTCTT | ATCAGGCCTA | CGGGTGACCG | ACAATGCCCG | 4567 |
| GAAGCGATAC | GAAATATTCG | GTCTACGGTT | TAAAAGATAA | CGATTACTGA | AGGATG | 4623 |

(2) INFORMATION FOR SEQ ID NO:8:

(i) SEQUENCE CHARACTERISTICS:
       (A) LENGTH: 933 amino acids
       (B) TYPE: amino acid
       (D) TOPOLOGY: linear (ii) MOLECULE TYPE: protein (xi) SEQUENCE DESCRIPTION: SEQ ID NO:8:

```
Met Gln Asn Ser Ala Leu Lys Ala Trp Leu Asp Ser Ser Tyr Leu Ser
 1               5                  10                  15
Gly Ala Asn Gln Ser Trp Ile Glu Gln Leu Tyr Glu Asp Phe Leu Thr
                20                  25                  30
Asp Pro Asp Ser Val Asp Ala Asn Trp Arg Ser Thr Phe Gln Gln Leu
            35                  40                  45
Pro Gly Thr Gly Val Lys Pro Asp Gln Phe His Ser Gln Thr Arg Glu
        50                  55                  60
Tyr Phe Arg Arg Leu Ala Lys Asp Ala Ser Arg Tyr Ser Ser Thr Ile
 65                  70                  75                  80
Ser Asp Pro Asp Thr Asn Val Lys Gln Val Lys Val Leu Gln Leu Ile
                85                  90                  95
Asn Ala Tyr Arg Phe Arg Gly His Gln His Ala Asn Leu Asp Pro Leu
               100                 105                 110
Gly Leu Trp Gln Gln Asp Lys Val Ala Asp Leu Asp Pro Ser Phe His
           115                 120                 125
Asp Leu Thr Glu Ala Asp Phe Gln Glu Thr Phe Asn Val Gly Ser Phe
       130                 135                 140
Ala Ser Gly Lys Glu Thr Met Lys Leu Gly Glu Leu Leu Glu Ala Leu
145                 150                 155                 160
Lys Gln Thr Tyr Cys Gly Pro Ile Gly Ala Glu Tyr Met His Ile Thr
               165                 170                 175
Ser Thr Glu Glu Lys Arg Trp Ile Gln Gln Arg Ile Glu Ser Gly Arg
           180                 185                 190
Ala Thr Phe Asn Ser Glu Glu Lys Lys Arg Phe Leu Ser Glu Leu Thr
       195                 200                 205
Ala Ala Glu Gly Leu Glu Arg Tyr Leu Gly Ala Lys Phe Pro Gly Ala
   210                 215                 220
Lys Arg Phe Ser Leu Glu Gly Gly Asp Ala Leu Ile Pro Met Leu Lys
225                 230                 235                 240
Glu Met Ile Arg His Ala Gly Asn Ser Gly Thr Arg Glu Val Val Leu
               245                 250                 255
Gly Met Ala His Arg Gly Arg Leu Asn Val Leu Val Asn Val Leu Gly
           260                 265                 270
Lys Lys Pro Gln Asp Leu Phe Asp Glu Phe Ala Gly Lys His Lys Glu
       275                 280                 285
His Leu Gly Thr Gly Asp Val Lys Tyr His Met Gly Phe Ser Ser Asp
   290                 295                 300
Phe Gln Thr Asp Gly Gly Leu Val His Leu Ala Leu Ala Phe Asn Pro
305                 310                 315                 320
```

|     |     |     |     |     |     |     |     |     |     |     |     |     |     |     |
|-----|-----|-----|-----|-----|-----|-----|-----|-----|-----|-----|-----|-----|-----|-----|
| Ser | His | Leu | Glu | Ile | Val | Ser | Pro | Val | Ile | Gly | Ser | Val | Arg | Ala |
|     |     |     |     | 325 |     |     |     | 330 |     |     |     | 335 |     |     |
| Arg | Leu | Asp | Arg | Leu | Asp | Glu | Pro | Ser | Ser | Asn | Lys | Val | Leu | Pro | Ile |
|     |     |     | 340 |     |     |     |     | 345 |     |     |     | 350 |     |     |
| Thr | Ile | His | Gly | Asp | Ala | Ala | Val | Thr | Gly | Gln | Gly | Val | Val | Gln | Glu |
|     |     | 355 |     |     |     | 360 |     |     |     | 365 |     |     |     |
| Thr | Leu | Asn | Met | Ser | Lys | Ala | Arg | Gly | Tyr | Glu | Val | Gly | Gly | Thr | Val |
|     | 370 |     |     |     | 375 |     |     |     | 380 |     |     |     |
| Arg | Ile | Val | Ile | Asn | Asn | Gln | Val | Gly | Phe | Thr | Thr | Ser | Asn | Pro | Leu |
| 385 |     |     |     | 390 |     |     |     | 395 |     |     |     | 400 |
| Asp | Ala | Arg | Ser | Thr | Pro | Tyr | Cys | Thr | Asp | Ile | Gly | Lys | Met | Val | Gln |
|     |     |     | 405 |     |     |     | 410 |     |     |     | 415 |
| Ala | Pro | Ile | Phe | His | Val | Asn | Ala | Asp | Asp | Pro | Glu | Ala | Val | Ala | Phe |
|     |     | 420 |     |     |     | 425 |     |     |     | 430 |
| Val | Thr | Arg | Leu | Ala | Leu | Asp | Phe | Arg | Asn | Thr | Phe | Lys | Arg | Asp | Val |
|     | 435 |     |     |     | 440 |     |     |     | 445 |     |     |
| Phe | Ile | Asp | Leu | Val | Ser | Tyr | Arg | Arg | His | Gly | His | Asn | Glu | Ala | Asp |
|     | 450 |     |     |     | 455 |     |     |     | 460 |     |     |
| Glu | Pro | Ser | Ala | Thr | Gln | Pro | Leu | Met | Tyr | Gln | Lys | Ile | Lys | Lys | His |
| 465 |     |     |     | 470 |     |     |     | 475 |     |     |     | 480 |
| Pro | Thr | Pro | Arg | Lys | Ile | Tyr | Ala | Asp | Lys | Leu | Glu | Gln | Glu | Lys | Val |
|     |     |     | 485 |     |     |     | 490 |     |     |     | 495 |
| Ala | Thr | Leu | Glu | Asp | Ala | Thr | Glu | Met | Val | Asn | Leu | Tyr | Arg | Asp | Ala |
|     |     |     | 500 |     |     |     | 505 |     |     |     | 510 |
| Leu | Asp | Ala | Gly | Asp | Cys | Val | Val | Ala | Glu | Trp | Arg | Pro | Met | Asn | Met |
|     |     | 515 |     |     |     | 520 |     |     |     | 525 |
| His | Ser | Phe | Thr | Trp | Ser | Pro | Tyr | Leu | Asn | His | Glu | Trp | Asp | Glu | Glu |
|     | 530 |     |     |     | 535 |     |     |     | 540 |     |     |
| Tyr | Pro | Asn | Lys | Val | Glu | Met | Lys | Arg | Leu | Gln | Glu | Leu | Ala | Lys | Arg |
| 545 |     |     |     | 550 |     |     |     | 555 |     |     |     | 560 |
| Ile | Ser | Thr | Val | Pro | Glu | Ala | Val | Glu | Met | Gln | Ser | Arg | Val | Ala | Lys |
|     |     |     | 565 |     |     |     | 570 |     |     |     | 575 |
| Ile | Tyr | Gly | Asp | Arg | Gln | Ala | Met | Ala | Ala | Gly | Glu | Lys | Leu | Phe | Asp |
|     |     |     | 580 |     |     |     | 585 |     |     |     | 590 |
| Trp | Gly | Gly | Ala | Glu | Asn | Leu | Ala | Tyr | Ala | Thr | Leu | Val | Asp | Glu | Gly |
|     |     | 595 |     |     |     | 600 |     |     |     | 605 |
| Ile | Pro | Val | Arg | Leu | Ser | Gly | Glu | Asp | Ser | Gly | Arg | Gly | Thr | Phe | Phe |
|     | 610 |     |     |     | 615 |     |     |     | 620 |     |     |
| His | Arg | His | Ala | Val | Ile | His | Asn | Gln | Ser | Asn | Gly | Ser | Thr | Tyr | Thr |
| 625 |     |     |     |     | 630 |     |     |     | 635 |     |     |     | 640 |
| Pro | Leu | Gln | His | Ile | His | Asn | Gly | Gln | Gly | Ala | Phe | Arg | Val | Trp | Asp |
|     |     |     | 645 |     |     |     | 650 |     |     |     | 655 |
| Ser | Val | Leu | Ser | Glu | Glu | Ala | Val | Leu | Ala | Phe | Glu | Tyr | Gly | Tyr | Ala |
|     |     |     | 660 |     |     |     | 665 |     |     |     | 670 |
| Thr | Ala | Glu | Pro | Arg | Thr | Leu | Thr | Ile | Trp | Glu | Ala | Gln | Phe | Gly | Asp |
|     |     | 675 |     |     |     | 680 |     |     |     | 685 |
| Phe | Pro | Asn | Gly | Ala | Gln | Val | Val | Ile | Asp | Gln | Phe | Ile | Ser | Ser | Gly |
|     |     | 690 |     |     |     | 695 |     |     |     | 700 |
| Glu | Gln | Lys | Trp | Gly | Arg | Met | Cys | Gly | Leu | Val | Met | Leu | Leu | Pro | His |
| 705 |     |     |     |     | 710 |     |     |     | 715 |     |     |     | 720 |
| Gly | Tyr | Glu | Gly | Gln | Gly | Pro | Glu | His | Ser | Ser | Ala | Arg | Leu | Glu | Arg |
|     |     |     |     | 725 |     |     |     | 730 |     |     |     | 735 |
| Tyr | Leu | Gln | Leu | Cys | Ala | Glu | Gln | Asn | Met | Gln | Val | Cys | Val | Pro | Ser |
|     |     |     | 740 |     |     |     | 745 |     |     |     | 750 |

| | | | | | | | | | | | | | | |
|---|---|---|---|---|---|---|---|---|---|---|---|---|---|---|
|Thr|Pro|Ala|Gln|Val|Tyr|His|Met|Leu|Arg|Arg|Gln|Ala|Leu|Arg|Gly|
| | |755| | | |760| | | | |765| | | |
|Met|Arg|Arg|Pro|Leu|Val|Val|Met|Ser|Pro|Lys|Ser|Leu|Leu|Arg|His|
| |770| | | |775| | | | |780| | | | |
|Pro|Leu|Ala|Val|Ser|Ser|Leu|Glu|Glu|Leu|Ala|Asn|Gly|Thr|Phe|Leu|
|785| | | | |790| | | |795| | | | |800|
|Pro|Ala|Ile|Gly|Glu|Ile|Asp|Glu|Leu|Asp|Pro|Lys|Gly|Val|Lys|Arg|
| | | | |805| | | |810| | | | |815| |
|Val|Val|Met|Cys|Ser|Gly|Lys|Val|Tyr|Tyr|Asp|Leu|Leu|Glu|Gln|Arg|
| | | |820| | | | |825| | | |830| | |
|Arg|Lys|Asn|Asn|Gln|His|Asp|Val|Ala|Ile|Val|Arg|Ile|Glu|Gln|Leu|
| | |835| | | |840| | | | |845| | | |
|Tyr|Pro|Phe|Pro|His|Lys|Ala|Met|Gln|Glu|Val|Leu|Gln|Gln|Phe|Ala|
|850| | | | |855| | | | |860| | | | |
|His|Val|Lys|Asp|Phe|Val|Trp|Cys|Gln|Glu|Glu|Pro|Leu|Asn|Gln|Gly|
|865| | | | |870| | | |875| | | | |880| |
|Ala|Trp|Tyr|Cys|Ser|Gln|His|His|Phe|Arg|Glu|Val|Ile|Pro|Phe|Gly|
| | | |885| | | | |890| | | | |895| | |
|Ala|Ser|Leu|Arg|Tyr|Ala|Gly|Arg|Pro|Ala|Ser|Ala|Ser|Pro|Ala|Val|
| | |900| | | |905| | | | |910| | | | |
|Gly|Tyr|Met|Ser|Val|His|Gln|Lys|Gln|Gln|Gln|Asp|Leu|Val|Asn|Asp|
| |915| | | | |920| | | | |925| | | | |
|Ala|Leu|Asn|Val|Glu| | | | | | | | | | | |
|930| | | | | | | | | | | | | | | |

(2) INFORMATION FOR SEQ ID NO:9:

(i) SEQUENCE CHARACTERISTICS:
(A) LENGTH: 405 amino acids
(B) TYPE: amino acid
(D) TOPOLOGY: linear (ii) MOLECULE TYPE: protein (xi) SEQUENCE DESCRIPTION: SEQ ID NO:9:

| | | | | | | | | | | | | | | |
|---|---|---|---|---|---|---|---|---|---|---|---|---|---|---|
|Met|Ser|Ser|Val|Asp|Ile|Leu|Val|Pro|Asp|Leu|Pro|Glu|Ser|Val|Ala|
|1| | | |5| | | | |10| | | | |15| |
|Asp|Ala|Thr|Val|Ala|Thr|Trp|His|Lys|Lys|Pro|Gly|Asp|Ala|Val|Val|
| | | |20| | | | |25| | | | |30| | |
|Arg|Asp|Glu|Val|Leu|Val|Glu|Ile|Glu|Thr|Asp|Lys|Val|Val|Leu|Glu|
| | |35| | | | |40| | | | |45| | | |
|Val|Pro|Ala|Ser|Ala|Asp|Gly|Ile|Leu|Asp|Ala|Val|Leu|Glu|Asp|Glu|
| |50| | | | |55| | | | |60| | | | |
|Gly|Thr|Thr|Val|Thr|Ser|Arg|Gln|Ile|Leu|Gly|Arg|Leu|Arg|Glu|Gly|
|65| | | | |70| | | | |75| | | | |80|
|Asn|Ser|Ala|Gly|Lys|Glu|Thr|Ser|Ala|Lys|Ser|Glu|Glu|Lys|Ala|Ser|
| | | | |85| | | | |90| | | | |95| |
|Thr|Pro|Ala|Gln|Arg|Gln|Gln|Ala|Ser|Leu|Glu|Glu|Gln|Asn|Asn|Asp|
| | | |100| | | | |105| | | | |110| | |
|Ala|Leu|Ser|Pro|Ala|Ile|Arg|Arg|Leu|Leu|Ala|Glu|His|Asn|Leu|Asp|
| | |115| | | | |120| | | | |125| | | |
|Ala|Ser|Ala|Ile|Lys|Gly|Thr|Gly|Val|Gly|Gly|Arg|Leu|Thr|Arg|Glu|
| |130| | | | |135| | | | |140| | | | |
|Asp|Val|Glu|Lys|His|Leu|Ala|Lys|Ala|Pro|Ala|Lys|Glu|Ser|Ala|Pro|
|145| | | | |150| | | | |155| | | | |160|
|Ala|Ala|Ala|Ala|Pro|Ala|Ala|Gln|Pro|Ala|Leu|Ala|Ala|Arg|Ser|Glu|

|   |   |   |   |   | 165 |   |   |   |   | 170 |   |   |   |   | 175 |   |
|---|---|---|---|---|---|---|---|---|---|---|---|---|---|---|---|---|

Lys Arg Val Pro Met Thr Arg Leu Arg Lys Arg Val Ala Glu Arg Leu
            180                     185                 190

Leu Glu Ala Lys Asn Ser Thr Ala Met Leu Thr Thr Phe Asn Glu Val
            195                     200                 205

Asn Met Lys Pro Ile Met Asp Leu Arg Lys Gln Tyr Gly Glu Ala Phe
    210                 215                 220

Glu Lys Arg His Gly Ile Arg Leu Gly Phe Met Ser Phe Tyr Val Lys
225             230                 235                     240

Ala Val Val Glu Ala Leu Lys Arg Tyr Pro Glu Val Asn Ala Ser Ile
            245                 250                 255

Asp Gly Asp Asp Val Val Tyr His Asn Tyr Phe Asp Val Ser Met Ala
            260                 265                 270

Val Ser Thr Pro Arg Gly Leu Val Thr Pro Val Leu Arg Asp Val Asp
        275                 280             285

Thr Leu Gly Met Ala Asp Ile Glu Lys Lys Ile Lys Glu Leu Ala Val
    290                 295             300

Lys Gly Arg Asp Gly Lys Leu Thr Val Glu Asp Leu Thr Gly Gly Asn
305                 310             315                 320

Phe Thr Ile Thr Asn Gly Gly Val Phe Gly Ser Leu Met Ser Thr Pro
            325                 330             335

Ile Ile Asn Pro Pro Gln Ser Ala Ile Leu Gly Met His Ala Ile Lys
            340             345                 350

Asp Arg Pro Met Ala Val Asn Gly Gln Val Glu Ile Leu Pro Met Met
        355                 360             365

Tyr Leu Ala Leu Ser Tyr Asp His Arg Leu Ile Asp Gly Arg Glu Ser
    370             375                 380

Val Gly Phe Leu Val Thr Ile Lys Glu Leu Leu Glu Asp Pro Thr Arg
385             390             395                 400

Leu Leu Leu Asp Val
            405

( 2 ) INFORMATION FOR SEQ ID NO:10:

( i ) SEQUENCE CHARACTERISTICS:
        ( A ) LENGTH: 1937 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Escherichia coli ( i x ) FEATURE:
        ( A ) NAME/KEY: CDS
        ( B ) LOCATION: 194..1537
        ( D ) OTHER INFORMATION: /note="Method of feature
            determination: E"

( x i ) SEQUENCE DESCRIPTION: SEQ ID NO:10:

CCGGGTGGCA AAACTTTAGC GTCTGAGGTT ATCGCAATTT GGTTATGAGA TTACTCTCGT    60

TATTAATTTG CTTTCCTGGG TCATTTTTTT CTTGCTTACC GTCACATTCT TGATGGTATA    120

GTCGAAAACT GCAAAAGCAC ATGACATAAA CAACATAAGC ACAATCGTAT TAATATATAA    180

GGGTTTTATA TCT ATG GAT CAG ACA TAT TCT CTG GAG TCA TTC CTC AAC        229
            Met Asp Gln Thr Tyr Ser Leu Glu Ser Phe Leu Asn
                    410              415

CAT GTC CAA AAG CGC GAC CCG AAT CAA ACC GAG TTC GCG CAA GCC GTT       277

|     |     |     |     |     |     |     |     |     |     |     |     |     |     |     |     |
| --- | --- | --- | --- | --- | --- | --- | --- | --- | --- | --- | --- | --- | --- | --- | --- |
| His | Val | Gln | Lys | Arg | Asp | Pro | Asn | Gln | Thr | Glu | Phe | Ala | Gln | Ala | Val |
|     |     |     | 420 |     |     |     | 425 |     |     |     |     |     | 430 |     |     |

```
CGT  GAA  GTA  ATG  ACC  ACA  CTC  TGG  CCT  TTT  CTT  GAA  CAA  AAT  CCA  AAA           325
Arg  Glu  Val  Met  Thr  Thr  Leu  Trp  Pro  Phe  Leu  Glu  Gln  Asn  Pro  Lys
     435                      440                     445

TAT  CGC  CAG  ATG  TCA  TTA  CTG  GAG  CGT  CTG  GTT  GAA  CCG  GAG  CGC  GTG           373
Tyr  Arg  Gln  Met  Ser  Leu  Leu  Glu  Arg  Leu  Val  Glu  Pro  Glu  Arg  Val
450                      455                     460                          465

ATC  CAG  TTT  CGC  GTG  GTA  TGG  GTT  GAT  GAT  CGC  AAC  CAG  ATA  CAG  GTC           421
Ile  Gln  Phe  Arg  Val  Val  Trp  Val  Asp  Asp  Arg  Asn  Gln  Ile  Gln  Val
                         470                     475                          480

AAC  CGT  GCA  TGG  CGT  GTG  CAG  TTC  AGC  TCT  GCC  ATC  GGC  CCG  TAC  AAA           469
Asn  Arg  Ala  Trp  Arg  Val  Gln  Phe  Ser  Ser  Ala  Ile  Gly  Pro  Tyr  Lys
               485                      490                     495

GGC  GGT  ATG  CGC  TTC  CAT  CCG  TCA  GTT  AAC  CTT  TCC  ATT  CTC  AAA  TTC           517
Gly  Gly  Met  Arg  Phe  His  Pro  Ser  Val  Asn  Leu  Ser  Ile  Leu  Lys  Phe
          500                      505                     510

CTC  GGC  TTT  GAA  CAA  ACC  TTC  AAA  AAT  GCC  CTG  ACT  ACT  CTG  CCG  ATG           565
Leu  Gly  Phe  Glu  Gln  Thr  Phe  Lys  Asn  Ala  Leu  Thr  Thr  Leu  Pro  Met
     515                      520                     525

GGC  GGT  GGT  AAA  GGC  GGC  AGC  GAT  TTC  GAT  CCG  AAA  GGA  AAA  AGC  GAA           613
Gly  Gly  Gly  Lys  Gly  Gly  Ser  Asp  Phe  Asp  Pro  Lys  Gly  Lys  Ser  Glu
530                      535                     540                          545

GGT  GAA  GTG  ATG  CGT  TTT  TGC  CAG  GCG  CTG  ATG  ACT  GAA  CTG  TAT  CGC           661
Gly  Glu  Val  Met  Arg  Phe  Cys  Gln  Ala  Leu  Met  Thr  Glu  Leu  Tyr  Arg
                         550                     555                          560

CAC  CTG  GGC  GCG  GAT  ACC  GAC  GTT  CCG  GCA  GGT  GAT  ATC  GGG  GTT  GGT           709
His  Leu  Gly  Ala  Asp  Thr  Asp  Val  Pro  Ala  Gly  Asp  Ile  Gly  Val  Gly
               565                      570                     575

GGT  CGT  GAA  GTC  GGC  TTT  ATG  GCG  GGG  ATG  ATG  AAA  AAG  CTC  TCC  AAC           757
Gly  Arg  Glu  Val  Gly  Phe  Met  Ala  Gly  Met  Met  Lys  Lys  Leu  Ser  Asn
     580                      585                     590

AAT  ACC  GCC  TGC  GTC  TTC  ACC  GGT  AAG  GGC  CTT  TCA  TTT  GGC  GGC  AGT           805
Asn  Thr  Ala  Cys  Val  Phe  Thr  Gly  Lys  Gly  Leu  Ser  Phe  Gly  Gly  Ser
     595                      600                     605

CTT  ATT  CGC  CCG  GAA  GCT  ACC  GGC  TAC  GGT  CTG  GTT  TAT  TTC  ACA  GAA           853
Leu  Ile  Arg  Pro  Glu  Ala  Thr  Gly  Tyr  Gly  Leu  Val  Tyr  Phe  Thr  Glu
610                      615                     620                          625

GCA  ATG  CTA  AAA  CGC  CAC  GGT  ATG  GGT  TTT  GAA  GGG  ATG  CGC  GTT  TCC           901
Ala  Met  Leu  Lys  Arg  His  Gly  Met  Gly  Phe  Glu  Gly  Met  Arg  Val  Ser
                         630                     635                          640

GTT  TCT  GGC  TCC  GGC  AAC  GTC  GCC  CAG  TAC  GCT  ATC  GAA  AAA  GCG  ATG           949
Val  Ser  Gly  Ser  Gly  Asn  Val  Ala  Gln  Tyr  Ala  Ile  Glu  Lys  Ala  Met
               645                      650                     655

GAA  TTT  GGT  GCT  CGT  GTG  ATC  ACT  GCG  TCA  GAC  TCC  AGC  GGC  ACT  GTA           997
Glu  Phe  Gly  Ala  Arg  Val  Ile  Thr  Ala  Ser  Asp  Ser  Ser  Gly  Thr  Val
          660                      665                     670

GTT  GAT  GAA  AGC  GGA  TTC  ACG  AAA  GAG  AAA  CTG  GCA  CGT  CTT  ATC  GAA           1045
Val  Asp  Glu  Ser  Gly  Phe  Thr  Lys  Glu  Lys  Leu  Ala  Arg  Leu  Ile  Glu
     675                      680                     685

ATC  AAA  GCC  AGC  CGC  GAT  GGT  CGA  GTG  GCA  GAT  TAC  GCC  AAA  GAA  TTT           1093
Ile  Lys  Ala  Ser  Arg  Asp  Gly  Arg  Val  Ala  Asp  Tyr  Ala  Lys  Glu  Phe
690                      695                     700                          705

GGT  CTG  GTC  TAT  CTC  GAA  GGC  CAA  CAG  CCG  TGG  TCT  CTA  CCG  GTT  GAT           1141
Gly  Leu  Val  Tyr  Leu  Glu  Gly  Gln  Gln  Pro  Trp  Ser  Leu  Pro  Val  Asp
                         710                     715                          720

ATC  GCC  CTG  CCT  TGC  GCC  ACC  CAG  AAT  GAA  CTG  GAT  GTT  GAC  GCC  GCG           1189
Ile  Ala  Leu  Pro  Cys  Ala  Thr  Gln  Asn  Glu  Leu  Asp  Val  Asp  Ala  Ala
               725                      730                     735

CAT  CAG  CTT  ATC  GCT  AAT  GGC  GTT  AAA  GCC  GTC  GCC  GAA  GGG  GCA  AAT           1237
```

-continued

```
His Gln Leu Ile Ala Asn Gly Val Lys Ala Val Ala Glu Gly Ala Asn
        740                 745                 750

ATG CCG ACC ACC ATC GAA GCG ACT GAA CTG TTC CAG CAG GCA GGC GTA      1285
Met Pro Thr Thr Ile Glu Ala Thr Glu Leu Phe Gln Gln Ala Gly Val
    755             760                 765

CTA TTT GCA CCG GGT AAA GCG GCT AAT GCT GGT GGC GTC GCT ACA TCG      1333
Leu Phe Ala Pro Gly Lys Ala Ala Asn Ala Gly Gly Val Ala Thr Ser
770             775                 780                 785

GGC CTG GAA ATG CCA CAA AAC GCT GCG CGC CTG GGC TGG AAA GCC GAG      1381
Gly Leu Glu Met Pro Gln Asn Ala Ala Arg Leu Gly Trp Lys Ala Glu
                790                 795                 800

AAA GTT GAC GCA CGT TTG CAT CAC ATC ATG CTG GAT ATC CAC CAT GCC      1429
Lys Val Asp Ala Arg Leu His His Ile Met Leu Asp Ile His His Ala
            805                 810                 815

TGT GTT GAG CAT GGT GGT GAA GGT GAG CAA ACC AAC TAC GTG CAG GGC      1477
Cys Val Glu His Gly Gly Glu Gly Glu Gln Thr Asn Tyr Val Gln Gly
        820                 825                 830

GCG AAC ATT GCC GGT TTT GTG AAG GTT GCC GAT GCG ATG CTG GCG CAG      1525
Ala Asn Ile Ala Gly Phe Val Lys Val Ala Asp Ala Met Leu Ala Gln
    835                 840                 845

GGT GTG ATT TAA GTTGTAAATG CCTGATGGCG CTACGCTTAT CAGGCCTACA          1577
Gly Val Ile *
850

AATGGGCACA ATTCATTGCA GTTACGCTCT AATGTAGGCC GGGCAAGCGC AGCGCCCCG    1637

GCAAAATTTC AGGCGTTTAT GAGTATTTAA CGGATGATGC TCCCCACGGA ACATTTCTTA   1697

TGGGCCAACG GCATTTCTTA CTGTAGTGCT CCCAAAACTG CTTGTCGTAA CGATAACACG   1757

CTTCAAGTTC AGCATCCGTT AACTTTCTGC GGACTCACGC GCGCAGCACT ATGCCAGTAA   1817

AGAAATCCCA TTTGACTATT TTTTGATAA TCTTCTTCGC TTTCGAACAA CTCGTGCGCC    1877

TTTCGAGAAG CAAGCATTAT ATAATGCCAG GCCAGTTCTT CTTCAATTGT CCCGTTTTGA   1937
```

( 2 ) INFORMATION FOR SEQ ID NO:11:

( i ) SEQUENCE CHARACTERISTICS:
        ( A ) LENGTH: 447 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
```

|     |     |     |     |     | 130 |     |     |     |     | 135 |     |     |     |     | 140 |     |     |     |     |
| --- | --- | --- | --- | --- | --- | --- | --- | --- | --- | --- | --- | --- | --- | --- | --- | --- | --- | --- | --- |
| Arg 145 | Phe | Cys | Gln | Ala | Leu 150 | Met | Thr | Glu | Leu | Tyr 155 | Arg | His | Leu | Gly | Ala 160 | | | | |
| Asp | Thr | Asp | Val | Pro 165 | Ala | Gly | Asp | Ile | Gly 170 | Val | Gly | Gly | Arg | Glu 175 | Val | | | | |
| Gly | Phe | Met | Ala 180 | Gly | Met | Met | Lys | Lys 185 | Leu | Ser | Asn | Asn | Thr 190 | Ala | Cys | | | | |
| Val | Phe | Thr 195 | Gly | Lys | Gly | Leu | Ser 200 | Phe | Gly | Gly | Ser | Leu 205 | Ile | Arg | Pro | | | | |
| Glu | Ala 210 | Thr | Gly | Tyr | Gly | Leu 215 | Val | Tyr | Phe | Thr | Glu 220 | Ala | Met | Leu | Lys | | | | |
| Arg 225 | His | Gly | Met | Gly | Phe 230 | Glu | Gly | Met | Arg | Val 235 | Ser | Val | Ser | Gly | Ser 240 | | | | |
| Gly | Asn | Val | Ala | Gln 245 | Tyr | Ala | Ile | Glu | Lys 250 | Ala | Met | Glu | Phe | Gly 255 | Ala | | | | |
| Arg | Val | Ile | Thr 260 | Ala | Ser | Asp | Ser | Ser 265 | Gly | Thr | Val | Val | Asp 270 | Glu | Ser | | | | |
| Gly | Phe | Thr 275 | Lys | Glu | Lys | Leu | Ala 280 | Arg | Leu | Ile | Glu | Ile 285 | Lys | Ala | Ser | | | | |
| Arg | Asp 290 | Gly | Arg | Val | Ala | Asp 295 | Tyr | Ala | Lys | Glu | Phe 300 | Gly | Leu | Val | Tyr | | | | |
| Leu 305 | Glu | Gly | Gln | Gln | Pro 310 | Trp | Ser | Leu | Pro | Val 315 | Asp | Ile | Ala | Leu | Pro 320 | | | | |
| Cys | Ala | Thr | Gln | Asn 325 | Glu | Leu | Asp | Val | Asp 330 | Ala | Ala | His | Gln | Leu 335 | Ile | | | | |
| Ala | Asn | Gly | Val 340 | Lys | Ala | Val | Ala | Glu 345 | Gly | Ala | Asn | Met | Pro 350 | Thr | Thr | | | | |
| Ile | Glu | Ala 355 | Thr | Glu | Leu | Phe | Gln 360 | Gln | Ala | Gly | Val | Leu 365 | Phe | Ala | Pro | | | | |
| Gly | Lys 370 | Ala | Ala | Asn | Ala | Gly 375 | Gly | Val | Ala | Thr | Ser 380 | Gly | Leu | Glu | Met | | | | |
| Pro 385 | Gln | Asn | Ala | Ala | Arg 390 | Leu | Gly | Trp | Lys | Ala 395 | Glu | Lys | Val | Asp | Ala 400 | | | | |
| Arg | Leu | His | His | Ile 405 | Met | Leu | Asp | Ile | His 410 | His | Ala | Cys | Val | Glu 415 | His | | | | |
| Gly | Gly | Glu | Gly 420 | Glu | Gln | Thr | Asn | Tyr 425 | Val | Gln | Gly | Ala | Asn 430 | Ile | Ala | | | | |
| Gly | Phe | Val 435 | Lys | Val | Ala | Asp | Ala 440 | Met | Leu | Ala | Gln | Gly 445 | Val | Ile | | | | | |